(12) United States Patent
Yoo

(10) Patent No.: US 12,266,451 B2
(45) Date of Patent: Apr. 1, 2025

(54) AI MOVEMENT-TRACING APPARATUS OF INFECTED ASYMPTOMATIC PEOPLE AND METHOD USING THE SAME

(71) Applicant: RESEARCH & BUSINESS FOUNDATION SUNGKYUNKWAN UNIVERSITY, Suwon-si (KR)

(72) Inventor: Jae-Chern Yoo, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 539 days.

(21) Appl. No.: 17/673,262

(22) Filed: Feb. 16, 2022

(65) Prior Publication Data

US 2022/0270765 A1  Aug. 25, 2022

(30) Foreign Application Priority Data

Feb. 23, 2021  (KR) .................. 10-2021-0024156

(51) Int. Cl.
| | |
|---|---|
| *G16H 50/80* | (2018.01) |
| *G06T 7/00* | (2017.01) |
| *G06V 40/12* | (2022.01) |
| *G10L 15/16* | (2006.01) |
| *G10L 15/22* | (2006.01) |
| *G10L 15/28* | (2013.01) |
| *G10L 25/51* | (2013.01) |

(Continued)

(52) U.S. Cl.
CPC ............ *G16H 50/80* (2018.01); *G06T 7/0012* (2013.01); *G06V 40/1365* (2022.01); *G10L 15/16* (2013.01); *G10L 15/22* (2013.01); *G10L 15/28* (2013.01); *G10L 25/51* (2013.01); *H04N 5/33* (2013.01); *H04W 4/029* (2018.02); *G06T 2207/10048* (2013.01); *G06T 2207/30004* (2013.01); *G06T 2207/30196* (2013.01); *G10L 2015/223* (2013.01); *G10L 2015/225* (2013.01)

(58) Field of Classification Search
CPC .............................. G16H 50/80; H04W 4/029
USPC ....................................................... 455/456.1
See application file for complete search history.

(56) References Cited

U.S. PATENT DOCUMENTS 11,342,051 B1 * 5/2022  Jain ....................... G16H 10/60

FOREIGN PATENT DOCUMENTS

KR  10-2020-0047457 A  5/2020

* cited by examiner

*Primary Examiner* — Ahmad F. Matar
*Assistant Examiner* — Jirapon Tulop
(74) *Attorney, Agent, or Firm* — NSIP Law

(57) ABSTRACT

The present disclosure provides an artificial intelligence-infected asymptomatic people movement-tracing apparatus and a method which in an emergency such as an epidemic pandemic, use an artificial intelligence movement-tracing apparatus of infected asymptomatic people of the present disclosure which is personally installed in the residence of the tracing target to automatically check whether to match the traffic line of the tracing target and the traffic line of the confirmed case and automatically report to the disease control authority only when the traffic lines match to protect individual privacy compared to the centralized system and automatically search for infected asymptomatic people classified as blind confirmed cases (hidden positive people) and self-quarantine subjects to quickly establish an infectious disease management system for suspected disease patients and efficiently manage the people from the spread of infectious diseases.

20 Claims, 9 Drawing Sheets

(51) Int. Cl.
*H04N 5/33* (2023.01)
*H04W 4/029* (2018.01)

(1)

(2)

(3)

AI MOVEMENT-TRACING APPARATUS OF INFECTED ASYMPTOMATIC PEOPLE AND METHOD USING THE SAME

CROSS-REFERENCE TO RELATED APPLICATIONS

This application claims the benefit under 35 USC 119(a) of Korean Patent Application No. 10-2021-0024156, filed on Feb. 23, 2021, at the Korean Intellectual Property Office, the entire disclosure of which is incorporated herein by reference for all purposes.

FIELD

The present disclosure provides an apparatus and a method which in an emergency such as an epidemic pandemic, use an artificial intelligence movement tracing apparatus of infected asymptomatic people of the present disclosure which is personally installed in the residence of a tracing target to automatically check whether to match the traffic line of the confirmed case and automatically report to the disease control authority only when the traffic line matches to protect individual privacy compared to the centralized system and automatically search for infected asymptomatic people classified as so-called blind confirmed cases (hidden positive-confirmed people) and self-quarantine subjects to quickly establish an infectious disease management system for suspected disease patients and efficiently manage the people from the spread of infectious diseases.

DESCRIPTION OF THE RELATED ART

Recently, as many people receive abundant medical benefits due to the recent increase in hospital infrastructure along with cutting-edge medical equipment technology, humanity has been promoting more happiness than in the past by extending lifespan and improving a quality of life.

However, when the global epidemic occurs, it is difficult to prevent the spread of the disease with the existing hospital infrastructure and medical services due to the development of transportation. Specifically, it takes a long time to discover and isolate people exposed to the infectious diseases so that the community is exposed to the risk of secondary and tertiary infections. Further, when the person who has been exposed to the infectious disease is unsuccessful in discovering and isolating, the infection situation will worsen, and it is difficult to prevent the spread of the epidemic.

In order to solve this problem, in recent years, Apple and Google have announced to provide an application programming interface (API) related to a contact tracing technology which can be used in cellular phones. According to this API, a specific anonymous code ID (hereinafter, referred to as a key code) which is periodically generated is exchanged between short-distance cellular phones by means of a Bluetooth beacon. The exchanged key codes are uploaded in a cloud server. When a confirmed case occurs, key codes of the cellular phones of people who test positive are identified to search and find close contact who have the matching key codes within a predetermined period (for example, within 14 days) from a cloud server to send a notice to the cellular phone of the close contact recommending a covid 19 test. This technique is a Bluetooth-based technique which exchanges data within 10 meters so that the contact can be more accurately found as compared with the base station-based position tracing method of the related art which has an error of 50 m to 100 m. However, there is a problem in that personal information on the cloud server can be leaked to the outside.

Further, when the key code which is exchanged between the cellular phone on the basis of the Bluetooth is used, it is difficult to find a secondary infectious person which is infected by touching an object after a predetermined period of time has elapsed after the infected person touches the object. Viruses such as SARS, which have 80% similarity to the novel coronavirus covid-19, are known to persist for 9 days on inanimate surfaces including metal, glass, and plastic.

Further, the Chinese and Korean authorities require QR (quick response) code authentication for visitors to easily trace the cluster infections generated in places where users have close contacts such as clubs, motels, and pubs.

According to the QR code authentication, when a specific visitor downloads a QR code as a cellular phone application and enters a shop, the visitor reports the downloaded QR code to automatically upload smartphone information together with the QR code to a public server. Thereafter, when a confirmed case occurs from the shop, the corresponding QR code is searched from the public server to easily find visitors of the corresponding shop.

However, the personal information and privacy information are loaded (uploaded) together to the public server by means of the QR code, so that when the information is leaked to the outside before destroying the information, there may be a personal privacy protection issue. Further, individual parties who want to hide the fact that they have visited places such as motels or entertainment establishments may refuse the QR code authentication. Further, it is difficult to check when the visitor left the visited shop so that when a confirmed case occurs, all the people who visited the shop on the same day are included in the quarantine candidate pool, which causes the pool of suspicious contacts to become excessively large.

The location tracking method using a GPS or mobile phone base station has a low location tracking precision, so that it is difficult to distinguish even buildings. Further, the access records of ordinary passersby are also handed over to the disease control authorities, which may cause a high risk of being misused for watching purposes.

A background art of the present disclosure is disclosed in Korean Unexamined Patent Application Publication No. 10-2020-0047457.

In the meantime, the present disclosure is continuation applications of Application No. 10-2020-0055019 (Ceiling AI health monitoring apparatus and remote medical diagnosis method using the same), Application No. 10-2020-0071282 (Self-quarantine monitoring apparatus and method using the same), and Application No. 10-2020-0086171 (Distributed movement tracing apparatus and method using the same).

Content of the Invention

Problem to be Solved

The present disclosure is provided to solve the above-described problems of the related art and for example, provides advantages in that when an epidemic infection spreads in a specific place, national authorities or disease control authorities provide traffic line information of a confirmed case to an AI-infected asymptomatic people movement-tracing apparatus of the present disclosure, the AI-infected asymptomatic people movement-tracing apparatus finds out whether to overlap a traffic line of the confirmed case and automatically reports to the disease control authorities when the traffic line overlaps to automatically confirm a tracing target as a subject of self-quarantine so that the spread of infectious diseases is quickly suppressed in an early stage and the subject of self-quarantine is automatically selected to be isolated without causing external exposure of the personal privacy. The tracing target who is selected to be self-quarantined will be isolated for a predetermined period (for example, 14 days).

Further, the AI-infected asymptomatic people movement-tracing apparatus of the present disclosure forms contact pools of confirmed cases by collecting only tracing targets whose traffic lines overlap the traffic lines of the confirmed cases with an infected asymptomatic people searching unit installed on a terminal of the disease control authority. At this time, the infected asymptomatic people searching unit not only automatically finds out the infected asymptomatic people by finding out an intersection between different contact pools of confirmed cases, but also additionally confirms and notifies them as subjects of self-quarantine.

The AI-infected asymptomatic people movement-tracing apparatus of the present disclosure is a personal property installed in the residence of the tracing target. Therefore, as compared with the centralized location tracking device of the related art, there is very little possibility that a large amount of private life will be exposed to the outside at once so that the personal privacy can be well protected. Furthermore, the AI-infected asymptomatic people movement-tracing apparatus of the present disclosure is distributed as a personally owned device, so that as compared with the centralized device, it is advantageous in that the load is not applied due to the location tracking operation. Further, the AI-infected asymptomatic people movement-tracing apparatus of the present disclosure finds out the infected asymptomatic people by the intersection between different contact pools of confirmed cases and automatically provides infectious disease infection route information propagated by the confirmed cases.

When the AI-infected asymptomatic people movement-tracing apparatus of the present disclosure is installed on the ceiling, it is most optimal to consistently monitor the tracing target so that it is preferable that the apparatus of the present disclosure has a structure to be incorporated with a ceiling-mounted air conditioner or a ceiling-mounted light fixture.

According to another aspect of the AI-infected asymptomatic people movement-tracing apparatus of the present disclosure, it may be combined with a voice recognition terminal which controls a digital TV (or a smart mirror) which provides various contents by high-speed internet connection using a voice instruction.

According to another aspect of the AI-infected asymptomatic people movement-tracing apparatus of the present disclosure, the AI-infected asymptomatic people movement-tracing apparatus may be embedded to be integrated with a digital TV or a smart mirror which provides various contents by high-speed internet connection.

However, objects to be achieved by various embodiments of the present disclosure are not limited to the technical objects as described above and other technical objects may be present.

As a technical means to achieve the above-described technical object, according to an aspect of the present disclosure, an artificial intelligence-infected asymptomatic people movement-tracing apparatus includes: a digital communication module which is installed in one region in a residence of a tracing target and provides communication with a disease control authority terminal or wireless communication connection with a cellular phone of the tracing target; a traffic line matching determining unit which compares confirmed case traffic line information and tracing target traffic line information to find out whether there is a route in which confirmed case traffic line information and tracing target traffic line information overlap; a controller which selects the tracing target as a subject of self-quarantine when there is a route in which confirmed case traffic line information and tracing target traffic line information overlap and controls the driving of the digital communication module to provide information about the selected subject of self-quarantine to the disease control authority terminal; a confirmed case contact pool which is installed in the disease control authority terminal to store only traffic line information of the tracing target which overlaps traffic line information of each of a plurality of confirmed cases; an infected asymptomatic people searching unit which finds an infected asymptomatic people by discovering an intersection between different confirmed case contact pools; and an infection route tracking unit which backwardly tracks the confirmed case contact pool to find out the infection route on the basis of information of the infected asymptomatic people included in the intersection.

the confirmed case traffic line information may include one or more location information selected from a GPS coordinate which is collectable from a confirmed case cellular phone, accessed base station information, a visit place QR code, a plurality of Key codes, a Bluetooth transmitter ID, and Wi-Fi ID access recording information and length of stay information on the traffic line of a confirmed case which is synchronized according to the location information.

Further, the tracing target traffic line information may include one or more location information selected from a GPS coordinate which is collectable from a tracing target cellular phone, accessed base station information, a visit place QR code, a plurality of Key codes, a Bluetooth transmitter ID, and Wi-Fi ID access recording information and length of stay information on the traffic line which is synchronized according to the location information.

Further, the artificial intelligence-infected asymptomatic people movement-tracing apparatus further includes: a traffic line tracing management application which is installed in the cellular phone of the tracing target and provides cellular phone location information to the digital communication module, the traffic line tracing management application may include a stay valid filter which extracts only the location information which is acquired for a predetermined time or longer, among a plurality of location information of the cellular phone of the trading target provided from the plurality of location information providing units as valid location information to cumulatively store the valid location information in the resident memory of the cellular phone of the tracing target.

The traffic line tracing management application may further include a communication connection checking unit which detects a key code by a short distance beacon, an ID of a Bluetooth transmitter, and a Wi-Fi ID of an access point (AP) from the cellular phone of the tracing target to store as location information of the tracing target on the resident memory.

Further, the plurality of location information providing units may include at least one of a GPS (global positioning system) which provides location data of the cellular phone using a satellite, a Bluetooth transmitter and a Bluetooth beacon which provide a unique ID of Bluetooth to the cellular phone, cellular phones of short-distance contacts which share Key codes (cellular phone identification information) by the Bluetooth beacon, an access point (AP) of a wireless LAN which provides a Wi-Fi ID to the cellular phone, a black and white grid pattern which provides a QR code of the visit place to the cellular phone, and a base station which provides mobile communication location information accessing the cellular phone and include a building address represented to be combined with building information provided by geographic information system (GIS) building-integrated information.

Further, the traffic line tracing management application may include a self-quarantine confirming unit which confirms the tracing target as a self-quarantine and the self-quarantine confirming unit may confirm the tracing target as a subject of self-quarantine when the controller or the disease control authority terminal provides self-quarantine subject confirmation notice information to the cellular phone of the tracing target who is determined as the subject of self-quarantine and the tracing target finishes a fingerprint authentication procedure for the notice information by means of the cellular phone.

In the meantime, according to another aspect of the present disclosure, an artificial intelligence-infected asymptomatic people movement-tracing apparatus includes: a voice recognition terminal which is installed in one region in a residence of a tracing target, connected to an external device, controls the external device by a voice instruction collected by a microphone and provides a voice feedback service through a speaker, the voice recognition terminal includes: a traffic line matching determining unit which compares traffic line information of a confirmed case and traffic line information of a tracing target to find out whether there is a route in which a traffic line of the tracing target overlaps a traffic line of the confirmed case; and a controller which selects the tracing target as a subject of self-quarantine when there is a route in which the traffic line information of the confirmed case and the traffic line information of the tracing target overlap and drives a digital communication module to transmit information about the selected subject of self-quarantine to a disease control authority terminal; the disease control authority terminal includes: a confirmed case contact pool which stores information of tracing targets having traffic lines which overlap the traffic line of the confirmed case from a plurality of voice recognition terminals; an infected asymptomatic people searching unit which finds an infected asymptomatic people by an intersection between confirmed case contact pools formed by different confirmed cases; and an infection route tracking unit which backwardly tracks the confirmed case contact pools to find out the infection route on the basis of information of the infected asymptomatic people included in the intersection, the cellular phone of the tracing target uploads cellular phone location information of the tracing target to the voice recognition terminal by connection with the digital communication module at every predetermined time.

Further, the confirmed case contact pool provides the traffic line information of the confirmed case to the plurality of voice recognition terminals, the plurality of voice recognition terminals checks whether the traffic line information of the confirmed case and the traffic line information of the tracing target match, and provides the tracing targets to the infected asymptomatic people searching unit when the traffic line information match, the infected asymptomatic people searching unit collects and stores the provided traffic line information to form a first cycle confirmed case contact pool and thereafter, provides the first cycle confirmed case contact pool to the plurality of voice recognition terminals, the plurality of voice recognition terminals checks whether the traffic line information matches between the provided first cycle confirmed case contact pool and the tracing target and reports tracing targets having matched traffic lines to the infected asymptomatic people searching unit, the infected asymptomatic people searching unit collects and stores the reported traffic line information to a second cycle confirmed case contact pool and repeats this step N times to obtain an N-th cycle confirmed case pool. At this time, the entire confirmed case contact pool may be generated by a union of first cycle to N-th cycle confirmed case contact pools.

Further, the voice recognition terminal includes: a body temperature check diagnosis unit which determines a body temperature suspicious target on the basis of information collected from the tracing target; and a fingerprint authentication unit which checks whether a fingerprint input from a fingerprint sensor matches a previously registered fingerprint of the tracing target to perform identity authentication, and the body temperature check diagnosis unit includes: a non-contact temperature sensor including a thermal imaging camera which detects a thermal radiation emitted from a body of the tracing target to provide a thermal image or an IR temperature sensor which detects an IR ray emitted from the body of the tracing target to measure a temperature; and a body temperature determining unit which determines as an abnormal temperature suspicious target on the basis of a measured temperature value of a patient from the non-contact temperature sensor.

Further, the cellular phone of the tracing target includes a building stay section setting unit, and the building stay section setting unit calculates a length of stay and a visit location that the cellular phone of the tracing target stays in a specific building by tracking location information provided from the location information providing unit and uploads cellular phone location information of the tracing target which is cumulatively stored in a resident memory of the cellular phone of the tracing target at a stay ending time of the specific building to a tracing target traffic line information memory.

Further, the cellular phone of the tracing target includes a building stay section setting unit, and the building stay section setting unit tracks a UUID (universally unique identifier) and a received signal strength indicator (RSSI) value provided from the Bluetooth beacon by Bluetooth communication connection between a Bluetooth beacon installed in one region of the building and the cellular phone of the tracing target which is staying in a Bluetooth beacon signal region to calculate a length of stay and a visit location that the cellular phone of the tracing target stays in a specific building and uploads cellular phone location information of the tracing target which is cumulatively stored in a resident memory of the cellular phone of the tracing target at a stay ending time of the specific building to a tracing target traffic line information memory.

Further, the cellular phone of the tracing target may include a Wi-Fi switching unit which forcibly temporally switches the cellular phone to a Wi-Fi mode whenever a location of the cellular phone of the tracing target in the unit of buildings is changed, to search for a Wi-Fi which is communicable with the cellular phone of the tracing target, collects searched Wi-Fi ID information, and stores location information of the cellular phone of the tracing target which is associated with the time information synchronized with the Wi-Fi ID information in the resident memory on the cellular phone.

Further, the cellular phone of the tracing target includes a Bluetooth switching unit and the Bluetooth switching unit forcibly temporally switches the cellular phone to a Bluetooth mode whenever a location of the cellular phone of the tracing target in the unit of buildings is changed, and then searches for a Bluetooth beacon which is communicable with the cellular phone of the tracing target, collects unique ID information of a searched Bluetooth transmitter, stores location information which is associated with time information synchronized with the unique ID information of the Bluetooth transmitter in a resident memory on the cellular phone.

Further, the voice recognition terminal includes: a medical data receiver which receives medical data measured from a plurality of medical devices by short-distance communication connection between the digital communication module and the plurality of medical devices; and an artificial intelligence neural network which has been deep-learning trained by learning medical data in advance, and the deep learning trained artificial intelligence neural network analyzes the medical data received by the medical data receiver to automatically determine whether a patient has a disease and a risk of the disease.

Further, the voice recognition terminal may include: a digital TV or a smart mirror to share a screen between a patient and a medical expert during the remote medical diagnosis, and the controller may control the driving of the digital TV or the smart mirror to determine the necessity of the remote medical diagnosis according to the health condition of the patient on the basis of the medical data analysis result provided from the artificial intelligence neural network and perform the remote medical diagnosis between the doctor and the patient.

According to another aspect of the present disclosure, an infected asymptomatic people movement-tracing method performed by an artificial intelligence-infected asymptomatic people movement-tracing apparatus includes: transmitting traffic line information of a tracing target stored in a resident memory on a cellular phone of the tracing target; transmitting confirmed case traffic line information by a disease control authority terminal when a confirmed case occurs; reporting the tracing target as a subject of self-quarantine to the disease control authority terminal when traffic line information of the tracing target and traffic line information of the confirmed case overlap; transmitting self-quarantine subject confirmation notice information to a cellular phone of the tracing target from the disease control authority terminal; confirming as a subject of self-quarantine when the tracing target finishes an authentication procedure for the notice information by a fingerprint authentication procedure provided to the cellular phone; automatically finding out infected asymptomatic people information on the basis of an intersection between a plurality of confirmed case contact pools; and figuring out an infection route by backwardly tracking infected asymptomatic information included in the intersection on the confirmed case contact pool and notifying additional confirmation to tracing targets included in the infection route as subjects of self-quarantine.

Further, an infected asymptomatic people movement-tracing method performed by an artificial intelligence infected asymptomatic people movement-tracing apparatus includes: allowing an infected asymptomatic people searching unit to distribute confirmed case traffic line information to a plurality of voice recognition terminals to form a confirmed case contact pool; searching an intersection between confirmed case contact pools generated by different confirmed cases; figuring out an infection route by backwardly tracing on each confirmed case contact pool, on the basis of the intersection between the confirmed case contact pools acquired in the searching; and selecting all tracing targets on the infection route as subjects of self-quarantine.

Further, the searching of an intersection includes: finding out a set Intersection_Index of a cycle (i, j) which generates the intersection; and finding out a cycle $(i_o, j_o)$ which generates a first intersection, the searching of the set Intersection_Index includes

```
Intersection....Index = [ ]
⎡  for i = 1: max(i)
|      ⎡  for j = 1:: max(j)
|      |      ⎡  if TP₁ⁱ(A) ∩TP₁ʲ(B) ≠ ϕ
|      |      |      include (i,j) in the set of Intersection_Index
|      |      ⎣  end
|      ⎣  end
⎣  end,
``` here, i of (i, j) included in n the Intersection_Index is a cycle of the confirmed case A contact pool at the time when the intersection is generated and j is a cycle of the confirmed case B contact pool at the time when the intersection is generated, and the finding out of a cycle $(i_o,j_o)$ that generates an intersection finds out at least one or more $(i_o,j_o)$ selected from $$(i_o, j_o) = \min_{i,j} \text{size}[TP_1^i(A) \cap TP_1^j(B)| \forall\ (i, j) \in \text{Intersection\_Index}],$$

$$(i_o, j_o) = \min_{i,j}\ [(i + j)|\forall\ (i, j) \in \text{Intersection\_Index}],$$

$$(i_o, j_o) = \min_{i,j}\ [\text{absolute}(i - j)|\forall\ (i, j) \in \text{Intersection\_Index}],$$

$$(i_o, j_o) = \min_{i,j}\ [\min(i, j)|\forall\ (i, j) \in \text{Intersection\_Index}],$$

or $$(i_o, j_o) = \min_{i,j}\ [\max(i, j)|\forall\ (i, j) \in \text{Intersection\_Index}],$$

here, $\forall(i,j)\in$ Intersection_Index refers to all (i, j) included in the set Intersection_Index, min(i,j) refers a minimum value between i and j, max(i,j) refers to a maximum value between i and j, absolute (i-j) refers an absolute value of (i-j), and size[$TP^i_1(A) \cap TP^i_1(B)$] refers to a size of the intersection formed between $TP^i_1(A)$ and $TP^i_1(B)$.

Further, values of variables max(i) and max(j) are increased in proportional to the increase of the confirmed cases, or increased in proportional to the increase of the confirmed cases whose infection routes are not known or increased in proportional to a basic reproduction number (basic reproductive ratio) R0 (R naught).

Further, the forming of a confirmed case contact pool includes: allowing an infected asymptomatic people searching unit to provide the traffic line information of the confirmed case to the plurality of voice recognition terminals, a plurality of voice recognition terminals to check whether the traffic line information of the confirmed case and the traffic line information of the tracing target match, and provide the tracing targets to the infected asymptomatic people searching unit when the traffic line information match; allowing the infected asymptomatic people searching unit to collect and store traffic line information of tracing targets provided in the providing to the infected asymptomatic people searching unit to form a first cycle confirmed case contact pool; providing the first cycle confirmed case contact pool to the plurality of voice recognition terminals, allowing the plurality of voice recognition terminals to check whether traffic line information between the first cycle confirmed case contact pool and the tracing target match to report the matched tracing targets to the infected asymptomatic people searching unit; allowing the infected asymptomatic people searching unit to collect and store traffic line information of the reported tracing targets to form a second cycle confirmed case contact pool; allowing the infected asymptomatic people searching unit to provide an (N−1)th cycle confirmed case contact pool to the plurality of voice recognition terminals, the plurality of voice recognition terminals to check whether the traffic line information of the confirmed case contact pool and the traffic line information of the tracing target match, and report the matched tracing targets to the infected asymptomatic people searching unit, and infected asymptomatic people searching unit to collect and store traffic line information of the traffic line information of the reported tracing targets to form an N-th cycle confirmed case contact pool; and generating an entire confirmed case pool by a union of the first cycle confirmed case contact pool to the N-th cycle confirmed case contact pool.

The above-described solving means are merely illustrative but should not be construed as limiting the present disclosure. In addition to the above-described embodiments, additional embodiments may be further provided in the drawings and the detailed description of the present disclosure.

Effects of the Invention

According to the above-described solving means of the present disclosure, the AI-infected asymptomatic people movement-tracing apparatus which is personally owned automatically reports to the disease control authorities only when the traffic line overlaps the traffic line of the confirmed case so that the subject of self-quarantine including the infected asymptomatic people are searched and found out in an early stage while safely protecting the personal privacy as compared with the centralized device to quickly build the infectious disease control system for suspected cases and efficiently control the suspected cases from the spread of the infectious diseases.

However, the effect which can be achieved by the present disclosure is not limited to the above-described effects, there may be other effects.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Figure 1:
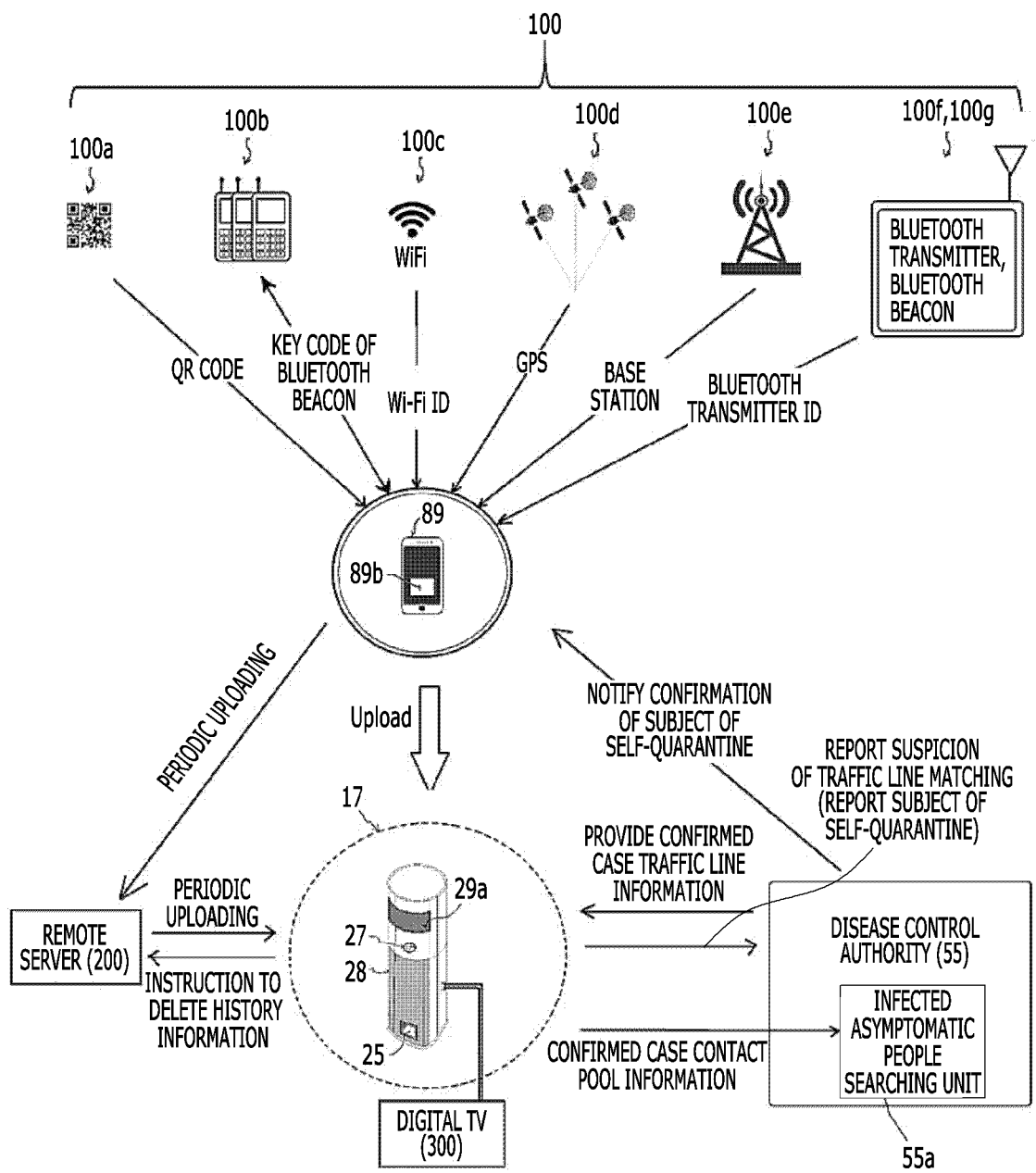
FIG. 1 is a view schematically illustrating an exemplary embodiment that an AI-infected asymptomatic people movement-tracing apparatus according to an exemplary embodiment of the present disclosure is not only connected to interwork with a digital TV (or a smart mirror) which provides various contents by high-speed Internet connection, but also is modified as a voice recognition terminal which controls the digital TV (or a smart mirror) by a voice instruction.

Hereinafter, the present disclosure will be described more fully hereinafter with reference to the accompanying drawings, in which exemplary embodiments of the present disclosure are shown. However, the present disclosure can be realized in various different forms, and is not limited to the embodiments described herein. Accordingly, in order to clearly explain the present disclosure in the drawings, portions not related to the description are omitted. Like reference numerals designate like elements throughout the specification.

Throughout this specification and the claims that follow, when it is described that an element is "coupled" to another element, the element may be "directly coupled" to the other element or "electrically coupled" or "indirectly coupled" to the other element through a third element.

Through the specification of the present disclosure, when one member is located "on", "above", "on an upper portion", "below", "under", and "on a lower portion" of the other member, the member may be adjacent to the other member or a third member may be disposed between the above two members.

In the specification of the present disclosure, unless explicitly described to the contrary, the word "comprise" and variations such as "comprises" or "comprising", will be understood to imply the inclusion of stated elements but not the exclusion of any other elements.

Hereinafter, an AI-infected asymptomatic people movement-tracing apparatus (not illustrated) of the present disclosure is also used as an infected asymptomatic people movement-tracing apparatus. Further, a cellular phone of the present disclosure can be used as a generic term (mixed) of a mobile terminal including a tablet PC.

In the present disclosure, a tracing target may refer to a user who resides in a residence where an infected asymptomatic people movement-tracing apparatus is installed and has registered Wi-Fi or Bluetooth connection to allow wireless communication between the infected asymptomatic people movement-tracing apparatus and its own cellular phone.

A patient in the present disclosure may also be used as a tracing target.

Movement history information in the present disclosure may also be used as location information.

Further, a cellular phone denoted by reference numeral 89 in the present disclosure may include all a cellular phone of a tracing target, a cellular phone of a subject of self-quarantine, and a cellular phone of a confirmed case.

In the present disclosure, a base station is a generic term including a repeater to support smooth communication network connection of a cellular phone. Further, in the present disclosure, Wi-Fi is a generic term including all units of wireless Internet. Furthermore, in the present disclosure, a Wi-Fi ID is a generic term including a service set identifier (SSID) and a media access control address (MAC). SSID is a unique ID name assigned to Internet routers which are currently installed in surroundings and is a value set to the Internet router.

The confirmed case in the present disclosure is a generic term including people who have been reliably diagnosed with a type or a condition of a disease by means of a disease measurement unit.

Further, in the present disclosure, a Bluetooth transmitter ID is a unique ID of a Bluetooth transmitter by which an address where the transmitter is installed is known and for example, may be a universally unique identifier (UUID).

FIG. 1 is a view schematically illustrating an exemplary embodiment that an AI-infected asymptomatic people movement-tracing apparatus of the present disclosure is not only connected to interwork with a digital TV 300 which provides various contents by high-speed Internet connection, but also is modified as a voice recognition terminal 17 which controls the digital TV 300 by a voice instruction.

In the exemplary embodiment, the digital TV 300 may be replaced with a smart mirror.

The smart mirror which is a display in which a mirror and a touch display are combined is a product manufactured by attaching a mirror film onto a display panel. The smart mirror looks like a mirror, but provide various functions such as time, weather, date, and a medical guide service for self-diagnosis by means of a touch display panel.

For example, FIG. 1 illustrates an exemplary embodiment that a traffic line tracing management application 89a installed (residing) in a cellular phone 89 of a tracing target in the form of an application cumulatively stores location information of the cellular phone 89 of the tracing target supplied from a plurality of location information providing units 100 in a resident memory 89b on the cellular phone of the tracing target and wirelessly transmits and uploads contents of the resident memory 89b to a voice recognition terminal 17 through short-distance communication whenever necessary or periodically wirelessly transmits cellular phone location information accumulated in the resident memory 89b to a remote server 200.

According to an exemplary embodiment of the present disclosure, the plurality of location information providing units 100 may include at least one of a GPS 100d which provides location data of the cellular phone 89 using a satellite, a Bluetooth transmitter 100f which provides a unique ID of Bluetooth to the cellular phone 89, a Bluetooth beacon 100g, neighboring cellular phones 100b which provide Key codes to the cellular phone 89 by the Bluetooth beacon, an AP 100c of a wireless LAN which provides a Wi-Fi ID to the cellular phone 89, a black and white grid pattern 100a which provides a QR code in a visit location to the cellular phone 89, and a base station (repeater) 100e which provides mobile communication location information accessing the cellular phone 89 of the tracing target.

Today, a GPS is widely used in navigators which find out an exact location of a current position and then compares map information stored by a geographic information system (GIS) to show a current location on the map. When a GPS satellite signal is used, signals are received from at least two or three GPS satellites to measure a location on the earth's surface using a difference between reception times. However, there is a disadvantage in that a GPS satellite signal is not well captured indoors so that it is not easy to accurately measure the location in a large building.

In the meantime, the plurality of location information providing units 100 prefers a building address expressed in combination with building information by a geographic information system (GIS) and integrated building information. The geographic information system building-integrated information is information which represents building information on map information and collectively refers to space (ground)-based building-integrated information built by combining building space information and building register attribute information in the unit of buildings on the basis of cadastral map information.

For example, the traffic line tracing management application 89a installed (residing) in the cellular phone 89 of the tracing target prefers to identify location data of the cellular phone by GPS (global positional system) location data using a satellite or cellular phone-accessed base station (repeater)-based geographic information and store synchronized time information in the memory 89b residing on the cellular phone 89 of the tracing target together with the identified location data.

According to an exemplary embodiment of the present disclosure, the cellular phone 89 of the tracing target may include a Wi-Fi switching unit. The Wi-Fi switching unit forcibly temporally switches the cellular phone to a Wi-Fi mode whenever a location of the cellular phone 89 of the tracing target in the unit of buildings is changed, to search for a Wi-Fi which is communicable with the cellular phone 89 of the tracing target. Further, the Wi-Fi switching unit collects searched Wi-Fi ID information to store location information of the cellular phone 89 of the tracing target which is interlinked with the Wi-Fi ID information and the synchronized time information in the resident memory 89b on the cellular phone.

In other words, the Wi-Fi switching unit searches for a connectable Wi-Fi in accordance with location information in the unit of buildings searched by the cellular phone 89 of the tracing target as the tracing target carries the cellular phone 89 of the tracing target and the tracing targets moves, and interlinks the searched Wi-Fi ID information and time information to be stored in the resident memory 89b as location information of the tracing target.

According to an exemplary embodiment of the present disclosure, the cellular phone 89 of the tracing target may include a Bluetooth switching unit. The Bluetooth switching unit forcibly temporally switches the cellular phone to a Bluetooth mode whenever a location of the cellular phone 89 of the tracing target in the unit of buildings is changed, to search for a Bluetooth beacon which is communicable with the cellular phone of the tracing target. Further, the Bluetooth switching unit may collect unique ID information of the searched Bluetooth transmitter. The Bluetooth switching unit may store location information associated with the unique ID information of the Bluetooth transmitter and synchronized time information in the resident memory 89b on the cellular phone.

For example, the Bluetooth switching unit searches for a connectable Bluetooth beacon in accordance with location information in the unit of buildings searched by the cellular phone 89 of the tracing target as the tracing target carries the cellular phone 89 of the tracing target and the tracing targets moves, and interlinks the searched unique ID information of the Bluetooth transmitter and time information to be stored in the resident memory 89b as location information of the tracing target.

Here, as the location change of the cellular phone of the tracing target in the unit of buildings, the change of the building address provided by the plurality of location information providing units of the present disclosure may be used.

Further, referring to FIG. 1, the voice recognition terminal 17 periodically reads traffic line history information of the tracing target from a remote server 200 to upload the traffic line history information of the tracing target in a storage space on the voice recognition terminal 17 and delete the traffic line history information of the tracing target stored in the remote server 200 after completely uploading.

Further, as another aspect, the voice recognition terminal 17 prefers to immediately read the traffic line history information of the tracing target from the remote server 200 to upload the information in the storage space as soon as the cellular phone location information accumulated in the resident memory 89b is transmitted to the remote server 200 and delete and discard the traffic line history information of the tracing target stored in the remote server 200 after completely uploading. In this case, the length of stay in which the traffic line history information of the tracing target remains in the remote server 200 may be minimized to prevent personal information leakage.

Further, as still another aspect, the voice recognition terminal 17 further prefers to use a cellular phone to voice recognition terminal communication mode in which cellular phone location information accumulated in the resident memory 89b is uploaded in the storage space on the voice recognition terminal 17 by direct wireless communication connection between the cellular phone 89 of the tracing target and the voice recognition terminal 17 without using the remote server 200. In this case, the voice recognition terminal 17 uploads the cellular phone location information stored on the resident memory 89b to the storage space on the voice recognition terminal 17 by wireless communication connection between the cellular phone 89 and the voice recognition terminal 17. It is preferable to automatically delete the cellular phone location information stored in the resident memory 89b after completely uploading.

For example, the cellular phone to voice recognition terminal communication mode provides advantages in that the traffic line history information of the tracing target stored in the resident memory 89b is directly stored in the storage space on the voice recognition terminal 17 without passing through the remote server 200 so that the personal information leakage can be completely prevented.

Further, it is preferable to periodically activate the cellular phone to voice recognition terminal communication mode when the cellular phone 89 of the tracing target is out of a normal activity range of the tracing target (for example, when the tracing target leaves the resident due to a business trip or vacation).

The tracing target may set an initial value of the activity range of the tracing target using the traffic line tracing management application 89a and the activity range prefers to be varied according to a life pattern of the tracing target on the basis of information provided from the plurality of location information providing unit 100.

For example, the initial value of the activity range is preferably a radius of 50 Km from the residence of the tracing target and the activity range beyond the initial value may be set by an average of lower limit activity ranges for four days among activity ranges of the cellular phone 89 of the tracing target for last 7 days on the basis of the current time.

Further, when a confirmed case occurs, a disease control authority terminal 55 provides traffic line information of the confirmed case to the voice recognition terminal 17 and the voice recognition terminal 17 determines whether the traffic lines of the confirmed case and the tracing target match. When the traffic lines match, the voice recognition terminal automatically reports to the disease control authority terminal 55 that the tracing target is a subject of self-quarantine (report suspicion of traffic line matching). In order words, the voice recognition terminal 17 determines whether traffic line information between the confirmed case and the tracing target match and when the traffic lines match (when there is an overlapping route), may provide information of the tracing target to the disease control authority terminal 55 as information about a subject of self-quarantine.

Further, the infected asymptomatic people searching unit 55a installed on the disease control authority terminal 55 collects and stores a list of tracing targets having traffic lines which match the traffic line of the confirmed case from the plurality of voice recognition terminals 17 to form a confirmed case contact pool. Thereafter, the infected asymptomatic people searching unit 55a automatically finds out the infected asymptomatic people by an intersection between the confirmed case contact pools formed by different confirmed cases and provides additional confirmation notice information to the infected asymptomatic people as subjects of self-quarantine.

Further, the infected asymptomatic people searching unit 55a installed on the disease control authority terminal 55 collects and stores tracing targets having traffic lines which match the traffic line of the confirmed case from the plurality of voice recognition terminals 17 to form a confirmed case contact pool. Thereafter, the infected asymptomatic people searching unit automatically finds out the infected asymptomatic people by the intersection between the confirmed case contact pools formed by different confirmed cases and backwardly tracks a source (an origin) of pools which generate the infected asymptomatic people belonging to the intersection by the infection route tracking unit to find out an infection route of the confirmed case.

Further, the disease control authority thoroughly analyzes the traffic line of the tracing target reported as a subject of self-quarantine and then when it is confirmed that the traffic line matches that of the confirmed case, notifies by sending a text message (notification information) informing that the tracing target is confirmed as a subject of self-quarantine to the cellular phone 80 of the tracing target determined as the self-quarantine by means of the disease control authority terminal 55.

Figure 2:
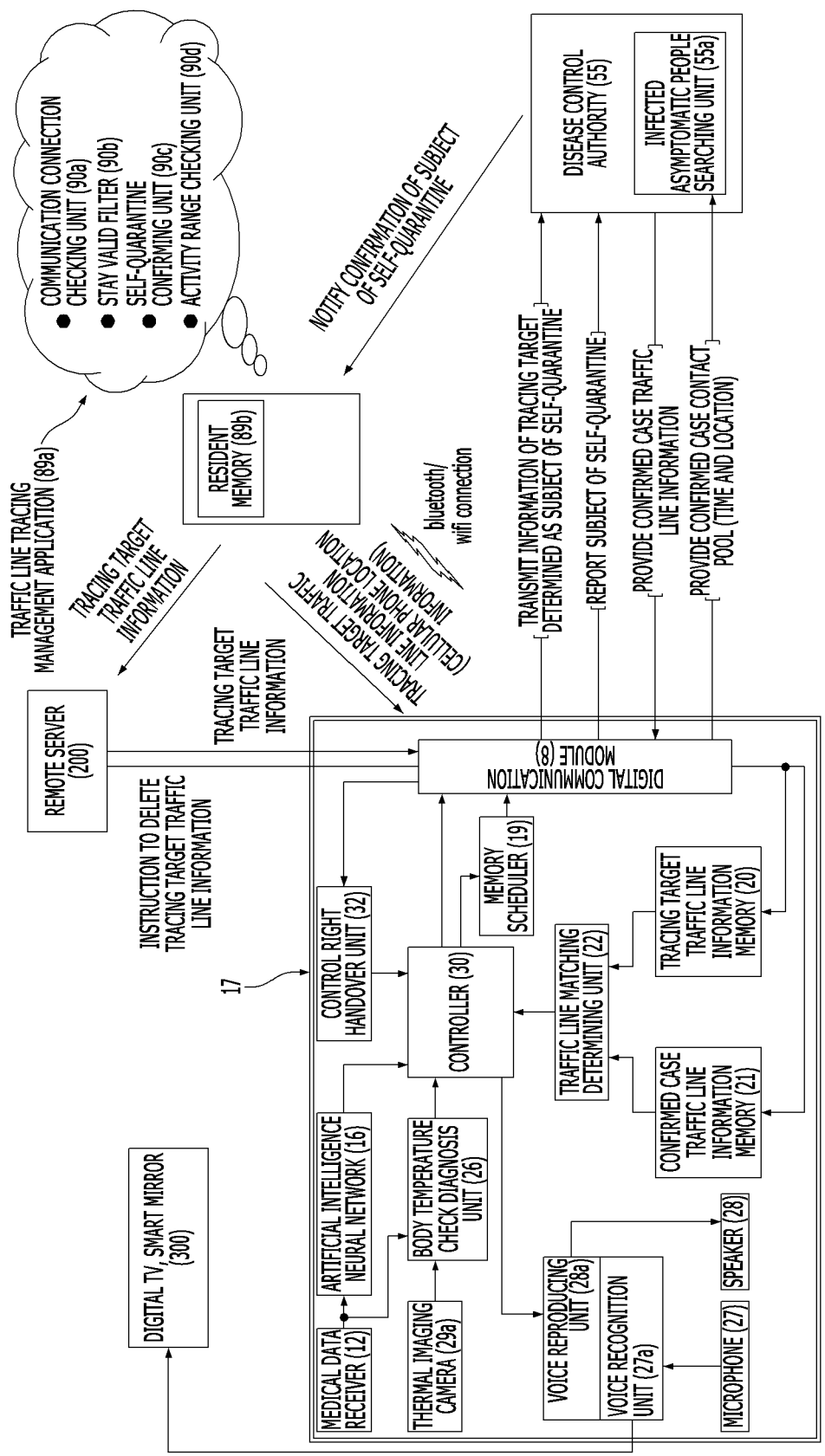
FIG. 2 is a view schematically illustrating another exemplary embodiment that an AI-infected asymptomatic people movement-tracing apparatus according to an exemplary embodiment of the present disclosure is modified as a voice recognition terminal which controls the digital TV (or a smart mirror) which provides various contents by high-speed Internet connection, by a voice instruction.

FIG. 2 is a view schematically illustrating another exemplary embodiment that an AI-infected asymptomatic people movement-tracing apparatus (not illustrated) according to an exemplary embodiment of the present disclosure is modified as a voice recognition terminal 17 which controls the digital TV 300 which provides various contents by high-speed Internet connection, by a voice instruction. In the exemplary embodiment, the digital TV 300 may be replaced with a smart mirror.

Referring to FIG. 2, the voice recognition terminal 17 may be provided in one region in the residence of the tracing target. Further, the voice recognition terminal 17 may include a digital communication module 8, a medical data receiver 12, an artificial intelligence neural network 16, a memory scheduler 19, a tracing target traffic line information memory 20, a confirmed case traffic line information memory 21, a traffic line matching determining unit 22, a body temperature check diagnosis unit 26, a microphone 27, a speaker 18, a controller 30, and a control right handover unit 32.

According to an exemplary embodiment of the present disclosure, the digital communication module 8 may provide communication with the disease control authority terminal 55, wireless communication connection with the cellular phone 89 of the tracing target, or short-distance communication (Bluetooth or Wi-Fi) connection with the cellular phone 89 of the tracing target.

Further, the tracing target traffic line information memory 20 may store traffic line history information of the tracing target cellular phone 89.

Further, the memory scheduler 19 may upload the cellular phone location information of the tracing target cumulatively stored in the resident memory 89b on the cellular phone of the tracing target to the tracing target traffic line information memory 20 by the connection with the digital communication module 8. Further, the memory scheduler 19 drives the digital communication module 8 to periodically (at every predetermined time) read the traffic line history information of the tracing target from the remote server 200 to upload the traffic line history information of the tracing target in the tracing target traffic line information memory 20 and delete the traffic line history information of the tracing target stored in the remote server 200 after completely uploading.

Further, the confirmed case traffic line information memory 21 may store traffic line information of the confirmed case provided from the disease control authority terminal 55 by means of the digital communication module 8.

Further, the traffic line matching determining unit 22 may compare the traffic line information (contents) of the confirmed case traffic line information memory 21 and the tracing target traffic line information memory 20 to find out whether the traffic line of the tracing target matches the traffic line of the confirmed case. In other words, the traffic line matching determining unit 22 may find out whether there is a route in which the traffic line of the tracing target matches the traffic line of the confirmed case by comparing the confirmed case traffic line information and the tracing target traffic line information.

For example, the traffic line matching determining unit 22 may compare a building address stored in the confirmed case traffic line information memory 21 and a building address stored in the tracing target traffic line information memory 20 and when the lengths of stay overlap according to the traffic lines, determines that the traffic line of the tracing target matches the traffic line of the confirmed case to classify the tracing target as a subject of self-quarantine.

In the case of outbreak of epidemic infection spread, the disease control authority terminal 55 may provide the traffic line information of the confirmed case to the confirmed case traffic line information memory 21 by means of the digital communication module 8. At this time, when the traffic line of the tracing target overlaps the traffic line of the confirmed case, the controller 30 may drive the digital communication module 8 to select the tracing target as the subject of self-quarantine to automatically transmit information about the selected subject of self-quarantine to the disease control authority terminal 55. Further, the control right handover unit 32 provides a means and a procedure for transferring the control right of the controller 30 to the disease control authority terminal 55.

According to the exemplary embodiment of the present disclosure, the control right handover unit 32 performs an approval process for allowing a tracing target to transfer a control right of the controller 30 of the infected asymptomatic people movement-tracing apparatus to the disease control authority terminal 55 according to the request of the disease control authority terminal 55 in the case of national emergency, particularly, in an emergency such as epidemic pandemic.

Further, when the control right of the infected asymptomatic people movement-tracing apparatus is transferred to the disease control authority terminal 55 and the traffic lines of the confirmed case and the tracing target match, the control right handover unit 32 allows the controller 30 to automatically report that the tracing target is a subject of self-quarantine to the disease control authority using the digital communication module 8.

Further, when the control right of the infected asymptomatic people movement-tracing apparatus is transferred to the disease control authority terminal and the tracing target is determined as a subject of self-quarantine, the control right handover unit 32 allows the disease control authority terminal 55 to read the recent traffic line history information of the tracing target stored in the tracing target traffic line information memory 20.

Furthermore, when the control right of the infected asymptomatic people movement-tracing apparatus is transferred to the disease control authority and the tracing target is determined as a subject of self-quarantine, the control right handover unit 32 allows the controller 30 to drive the digital communication module 8 to transmit the recent traffic line history information of the tracing target stored in the tracing target traffic line information memory 20 to the disease control authority terminal.

When the tracing target is determined as a subject of self-quarantine, contents to be transmitted to the disease control authority terminal 55 may be a digitalized message signal including information of the tracing target determined as a subject of self-quarantine (for example, traffic line history information stored in the tracing target traffic line information memory 20, a residence address, a name, an age, gender, a cellular phone number, an e-mail address, and a resident registration number). In the meantime, the control right handover approval process is preferably performed by the traffic line tracing management application 89a on the tracing target cellular phone 89. The disease control authority terminal 55 requests the handover of the control right, the tracing target accepts the request on the traffic line tracing management application 89*a* by fingerprint authentication. Thereafter, preferably, the traffic line tracing management application 89*a* simultaneously notifies that the control right handover is finished to the controller 30 by the wireless communication with the digital communication module 8 and activates the memory scheduler 19 to finish the control right handover approval procedure.

According to the exemplary embodiment of the present disclosure, when the tracing target is determined as a subject of self-quarantine, the controller 30 drives the digital communication module 8 to transmit and report information of the tracing target determined as a subject of self-quarantine (for example, traffic line history information stored in the tracing target traffic line information memory 20, a residence address, a name, an age, gender, a cellular phone number, an e-mail address, and a resident registration number) to the disease control authority terminal 55. At this time, the disease control authority thoroughly analyzes the traffic line information of the tracing target and then when the matching with the traffic line of the confirmed case is confirmed, transmits (provides) notification (information) indicating the confirmation of the subject of self-quarantine to the cellular phone 89 of the tracing target through the disease control authority terminal 55.

Further, when the memory scheduler 19 drives the digital communication module 8 to read traffic line information of the tracing target from the remote server 200 at every predetermined time (in a regular time interval) to upload the traffic line information in the tracing target traffic line information memory 20, the memory scheduler immediately deletes recorded contents of the remote server 200 for private privacy protection.

For example, a periodic reading time interval (every predetermined time) of the remote server 200 is preferably approximately 30 minutes and in this case, a deleting time interval of the recorded contents of the remote server 200 is also approximately 30 minutes so that the time in which the private information remains on the remote server 200 may be minimized.

The reference numeral 89*a* is a traffic line tracing management application which not only resides (is installed) in the cellular phone 89 of the tracing target in the form of an application, but also cumulatively stores the location information of the tracing target cellular phone 89 provided from the plurality of location information providing unit 100 in the resident memory 89*b* on the cellular phone and if necessary, wirelessly transmits the contents of the resident memory 89*b* to the digital communication module 8 or periodically wirelessly transmits the cellular phone location information (traffic line information of the tracing target) cumulatively stored in the resident memory 89*b* to the remote server 200.

According to the exemplary embodiment of the present disclosure, the traffic line tracing management application 89*a* may include a communication connection checking unit 90*a*, a stay valid filter 90*b*, a self-quarantine confirming unit 90*c*, and an activity range checking unit 90*d*.

The communication connection checking unit 90*a* is preferably installed in the traffic line tracing management application 89*a* to transmit cellular phone location information cumulatively stored in the resident memory 89*b* on the cellular phone 89 to the digital communication module 8 whenever the tracing target leaves the residence and then re-enters the residence.

For example, when a short-distance communication (Bluetooth or Wi-Fi) connection strength between the cellular phone 89 and the digital communication module 8 is equal to or lower than a predetermined value, the communication connection checking unit 90*a* preferably determines that the communication is disconnected and when a connection signal strength is increased to a predetermined reference or higher after a predetermined time is elapsed, determines that the tracing target re-enters the residence.

That is, the communication connection checking unit 90*a* checks the short-distance communication connection strength between the cellular phone 89 of the tracing target and the digital communication module 8 and when the connection signal strength is reduced a reference value or lower or connection attempt fails, determines that the tracing target leaves the residence.

Further, after the short-distance communication connection signal strength is reduced a reference value or lower or connection attempt fails, when the short-distance communication connection signal strength is increased to a reference or higher after a predetermined time (for example, 15 minutes or longer), the communication connection checking unit may determine that the tracing target re-enters the residence.

Further, the communication connection checking unit 90*a* may detect a new short-distance beacon signal (Key code) for example, a Bluetooth beacon signal, an IR beacon signal, or an ultrasonic beacon signal) from a neighbor of the cellular phone 89, a new ID from the Bluetooth transmitter 100*f*, or a new Wi-Fi ID, and store or register the signals or the ID on the resident memory 89*b* as cellular phone location information.

Further, the activity range checking unit 90*d* prefers to be installed in the traffic line tracing management application 89*a* and when the cellular phone 89 of the tracing target is determined to be out of the designated normal activity range, prefers to transmit location information cumulatively stored in the resident memory 89*b* on the cellular phone to the digital communication module 8 at every predetermined time (periodically) by means of the cellular phone to voice recognition terminal communication mode.

According to the exemplary embodiment of the present disclosure, as location ID (a Bluetooth transmitter ID, UUID, a Wi-Fi ID, a QR code) information, a building address expressed in the combination of building information by GIS building-integrated information is preferred. By doing this, the location ID (a Bluetooth transmitter ID, UUID, a Wi-Fi ID, a QR code) information may be converted into a building address in the unit of buildings or floor levels of the building.

Further, the stay valid filter 90*b* is preferably installed in the traffic line tracing management application 89*a* and when the same Wi-Fi ID is generated more than a predetermined number of times per hour, the stay valid filter 90*b* selects the Wi-Fi ID codes which are generated more than a predetermined number of times as valid Wi-Fi ID information to accumulate and store the Wi-Fi ID codes in the resident memory 89*b* of the tracing target cellular phone.

Further, when the same Bluetooth transmitter ID is generated more than a predetermined number of times per hour, the stay valid filter 90*b* selects the Bluetooth transmitter IDs which are generated more than a predetermined number of times as valid Bluetooth transmitter ID information to accumulate and store the Bluetooth transmitter ID in the resident memory 89*b* of the tracing target cellular phone.

Further, the stay valid filter 90*b* collects Key codes which are periodically generated a predetermined number of times from cellular phones in the vicinity of the tracing target to store the Key codes and time information synchronized therewith in the resident memory 89*b* on the cellular phone.

The Key code of the present disclosure is stored in the resident memory 89b on the cellular phone, rather than on a cloud server so that the personal privacy may be protected.

The self-quarantine confirming unit 90c according to the exemplary embodiment of the present disclosure is installed in the traffic line tracing management application 89a and may finish a confirmation notifying procedure of a subject of self-quarantine when the disease control authority terminal 55 issues a notice (confirmation notice information) informing that the tracing target is confirmed as a subject of self-quarantine to the cellular phone 89 of the tracing target who is determined as the subject of self-quarantine and the tracing target opens the notice (confirmation notice information) by a fingerprint authentication procedure on the cellular phone 89. The notice (confirmation notice information) includes rules to be followed as a self-quarantine.

Further, the self-quarantine confirming unit 90c allows the subject of self-quarantine to smoothly use the cellular phone by disappearing the notice from a screen of the cellular phone 89 only when the subject of self-quarantine opens the notice (confirmation notice information) by the fingerprint authentication procedure and then presses a confirmation button confirming to read and understand the notice, otherwise, the notice (confirmation notice information) is left on the screen of the cellular phone 89, which causes the inconvenience to use the cellular phone.

Further, the self-quarantine confirming unit 90c includes a return deadline timer so that after the subject of self-quarantine opens the notice by the fingerprint authentication procedure, a distance to the residence of the subject of self-quarantine is calculated on the basis of current location information of the cellular phone of the subject of self-quarantine provided from the location information providing unit 100 to provide information about residence return deadline to the self-quarantine and starts the counting of the return deadline timer.

The return deadline timer setting time is desirably selected in consideration of a transportation means used by the subject of self-quarantine to return. For example, it is desirable to consider the calculated distance to the residence and the surrounding transportation means (for example, subways, taxis, buses, walking, or a privately-owned car).

The return deadline timer is effective to solve the problem that the subject of self-quarantine wanders around several places to spread the infectious diseases throughout society in spite of the confirmation as the subject of self-quarantine.

According to the exemplary embodiment of the present disclosure, the voice recognition terminal 17 is connected to interwork with the digital TV 300 which provides various contents by high-speed internet connection, includes a voice recognition unit 27a and a voice reproducing unit 28a, controls the digital TV 300 by voice instruction collected by the microphone 27, and is provided with a voice feedback service by the speaker 28.

According to the exemplary embodiment of the present disclosure, when the control right of the controller 30 of the infected asymptomatic people movement-tracing apparatus (not illustrated) is transferred to the disease control authority terminal 55, the memory scheduler 19 reads location information of the cellular phone 89 of the tracing target cumulatively stored in the resident memory 89b on the cellular phone by short-distance communication connection (Wi-Fi or Bluetooth) between the cellular phone 89 of the tracing target and the digital communication module 8 to upload the location information in the tracing target traffic line information memory 20. The information is preferably uploaded whenever the communication connection checking unit 90a determines that the cellular phone 89 of the tracing target re-enters the residence.

According to another aspect of the memory scheduler 19, whenever the cellular phone location information stored on the resident memory 89b is updated or at every time interval, the memory scheduler drives the digital communication module 8 to generate the wireless communication connection (cellular phone to voice recognition terminal communication mode) between the cellular phone 89 and the voice recognition terminal 17 and at this time, reads the cellular phone location information stored on the resident memory 89b to upload the location information in the tracing target traffic line information memory 20 of the voice recognition terminal 17. After completely uploading, the traffic line tracing management application 89a preferably deletes the cellular phone location information which has been stored in the resident memory 89b. As described above, the traffic line tracing management application 89a deletes the cellular phone location information which has been stored in the resident memory 89b so that the privacy of the tracing target may be protected as much as possible.

According to another aspect of the memory scheduler 19, when the control right of the infected asymptomatic people movement-tracing apparatus (not illustrated) is transferred to the disease control authority terminal 55, the memory scheduler drives the digital communication module 8 to communicably connect to the remote server 200 and read the traffic line history information of the tracing target from the remote server 200 at every predetermined time (periodically) to upload the traffic line history information in the tracing target traffic line information memory 20 and issue an instruction to the remote server 200 to delete the contents of the remote server after completely uploading.

The memory scheduler 19 deletes the traffic line history information of the tracing target stored in the remote server 200 so that the privacy of the tracing target can be protected.

In the meantime, the memory scheduler 19 may periodically delete the contents stored in the tracing target traffic line information memory 20 after an expiration period (for example, four weeks or more after initially storing) has passed. The memory scheduler 19 periodically deletes the traffic line history information of the tracing target stored in the tracing target traffic line information memory 20 so that the privacy of the tracing target can be protected.

Further, when the control right of the infected asymptomatic people movement-tracing apparatus transferred to the disease control authority is canceled (erased), the memory scheduler 19 automatically deletes all contents stored in the remote server 200 and the tracing target traffic line information memory 20.

Further, the voice recognition terminal 17 includes the digital communication module 8 which provides short-distance communication connection (for example, Bluetooth connection) with medical devices, a medical data receiver 12 which receives medical data measured from patients by the medical devices by means of the digital communication module 8, and the artificial intelligence neural network 16 which is deep-learning trained in advance by the medical data for learning.

According to the exemplary embodiment of the present disclosure, the voice recognition terminal 17 not only is connected to interwork with the digital TV 300 which provides various contents by the high-speed internet connection, but also performs remote medical diagnosis through a doctor monitor 206 provided in a hospital by controlling the digital TV 300 with a voice instruction. In the exemplary embodiment, the digital TV 300 may be replaced with a smart mirror.

Further, the voice recognition terminal 17 may include the digital communication module 8 which provides Internet and Wi-Fi communication connection to allow remote medical diagnosis with a medical specialist or provide short-distance communication connection (Bluetooth connection) with a medical device.

Further, the voice recognition terminal 17 may include the digital TV 300 to share a screen between the patient and the medical specialist during the remote medical diagnosis.

Further, the voice recognition terminal 17 may include a medical data receiver 12 which receives medical data information measured from the patient by the medical device (not illustrated).

Further, the voice recognition terminal 17 may include the artificial intelligence neural network 16 which is deep-learning trained by the medical data for learning which is collected in advance by the medical device.

Further, the voice recognition terminal 17 may include the speaker 28 which provides guidelines for health care, a remote medical diagnosis method, and a guideline for how to use the medical device to the patient.

In the meantime, the voice recognition terminal 17 applies medical data of a patient which is measured and collected from the plurality of medical devices to the deep learning trained artificial intelligence neural network 16 to automatically determine whether the patient has a disease or the risk of the disease.

Further, the controller 30 controls the digital communication module 8, the speaker 28, and the digital TV 300 to provide the guideline for healthcare and a guideline about how to use the medical device to the patient according to the health condition of the patient with the medical data analysis result from the artificial intelligence neural network 16 as voice and image services.

Further, the controller 30 controls the digital communication module 8, the speaker 28, and the digital TV 300 to determine the necessity of the remote medical diagnosis according to the health condition of the patient with the medical data analysis result from the artificial intelligence neural network 16 and if necessary, perform the remote medical diagnosis between the doctor and the patient.

According to the exemplary embodiment of the present disclosure, the plurality of medical devices is a device including a wireless transmitter (for example, a Bluetooth transmitter) which transmits medical data measured from a specimen or an affected part of the patient to the medical data receiver 12 and may include at least one selected from an ultrasound scanner, a heart pulse sensor, a stethoscope, a thermal imaging camera, a temperature sensor, a urine tester, a toilet-installed stool tester, a breast cancer tester, a blood pressure monitor, a blood sugar monitor, a weight scale, a body fat analyzer, an image sensor showing sore throat or tooth condition, an eye ball (eye) test measuring device, an automated blood analyzer, a DNA amplification test device, a virus diagnostic kit device that diagnoses using virus specific antigen, a rapid test device using biomarker, a wearable device, a cancer diagnostic device, and a point of care testing (POCT) device.

Further, the voice recognition terminal 17 may further include a thermal imaging camera 29a which provides a thermal image which detects thermal radiation emitted from a body of the tracing target and shows a body temperature as a two-dimensional image and a body temperature check diagnosis unit 26.

For example, the body temperature check diagnosis unit 26 may include a face recognizing unit which recognizes a face of the tracing target and a body temperature determining unit (not illustrated) which measures a temperature value from pixels of a thermal image corresponding to a forehead area of the face and determines a person having an abnormal body temperature as a suspected target having an abnormal body temperature.

The thermal imaging camera 29a prefers to obtain the image of the image sensor to be overlaid with the thermal image. In this case, the image information from the image sensor is advantageous for face recognition because an outline boundary and the details are better expressed and when the body temperature is measured, the thermal image pixel corresponding to the forehead part may be more precisely selected.

The thermal imaging camera 29a may be replaced with a non-contact temperature sensor including an IR temperature sensor which detects an infrared ray emitted from a body (for example, a wrist or a forehead) of the tracing target to measure the temperature.

According to another aspect of the body temperature check diagnosis unit 26, the body temperature check diagnosis unit 26 may include a body temperature determining unit which determines a patient as a suspected target having an abnormal body temperature when a temperature of the patient collected by the medical data receiver 12 by means of the digital communication module 8 which provides the short-distance communication connection (for example Bluetooth connection) with the temperature sensor is an abnormal body temperature.

Further, the infected asymptomatic people searching unit 55a installed on the disease control authority terminal 55 collects and stores tracing targets having traffic lines which match the traffic line of the confirmed case from the voice recognition terminal 17 to form a confirmed case contact pool. Thereafter, the infected asymptomatic people searching unit 55a automatically finds out the infected asymptomatic people by the intersection between the confirmed case contact pools formed by different confirmed cases and backwardly tracks a source (an origin) of pools which generate the infected asymptomatic people belonging to the intersection by the infection route tracking unit to find out an infection route of the confirmed case.

The confirmed case contact pool of the present disclosure collectively refers to a set of tracing targets having traffic lines which overlap the traffic line of the confirmed case and the infected asymptomatic people searching unit 55a installed on the disease control authority terminal 55 distributes the confirmed case traffic line information to the plurality of voice recognition terminals 17. The voice recognition terminals 17 confirm whether the provided confirmed case traffic line information matches the tracing target traffic line information and if the information matches, report the fact to the infected asymptomatic people searching unit 55a and the infected asymptomatic people searching unit 55a collects and stores the reports to form the confirmed case contact pool.

Desirably, during the process of forming the confirmed case contact pool, the confirmed case traffic line information distributed to the voice recognition terminal 17 by the infected asymptomatic people searching unit 55a may include a beacon Key code of the confirmed case's cellular phone or Key codes collected by the confirmed case's cellular phone.

Desirably, during the process of forming the confirmed case contact pool, the tracing target traffic line information reported to the infected asymptomatic people searching unit 55a by the voice recognition terminal 17 may include Key codes collected by the cellular phone of the tracing target matching the distributed confirmed case traffic line information.

The confirmed case contact pool of the present disclosure includes time and location information of the tracing targets having the traffic line overlapping that of the confirmed case.

FIGS. 3A to 3D illustrate an exemplary embodiment that forms contact pools of confirmed cases by collecting and storing tracing targets whose traffic lines overlap a traffic line of a confirmed case from voice recognition terminals 17 by an infected asymptomatic people searching unit 55a installed on a disease control authority terminal 55, automatically finds out infected asymptomatic people by an intersection between contact pools of confirmed cases formed by different confirmed cases, backwardly tracks a source of pools which generate the infected asymptomatic people by an infection route tracking unit (not illustrated) to find out an infection route of the confirmed case.

Figure 3A:
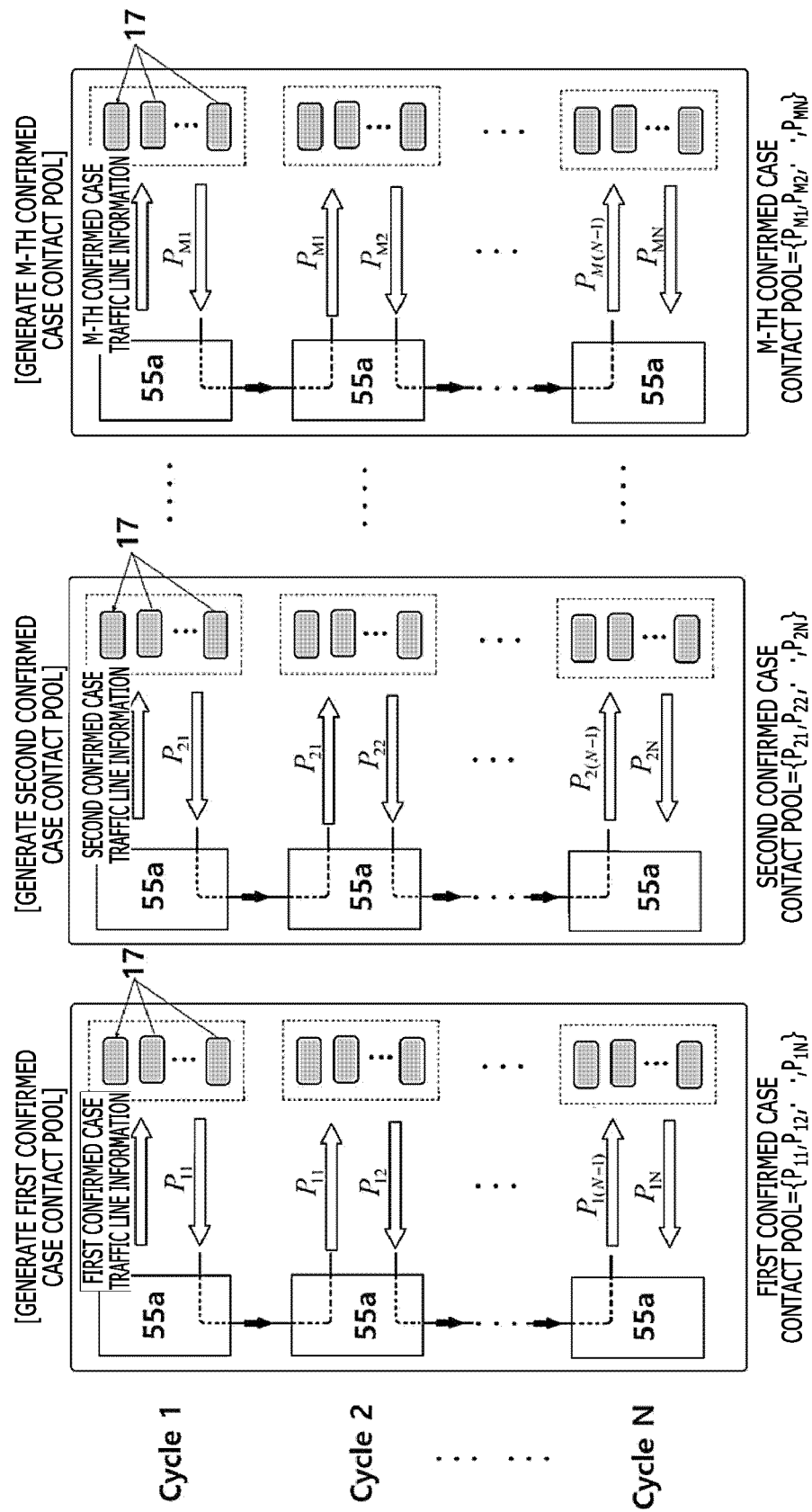
FIGS. 3A to 3D illustrate an exemplary embodiment that forms contact pools of confirmed cases by collecting and storing tracing targets whose traffic lines overlap a traffic line of a confirmed case from voice recognition terminals by an infected asymptomatic people searching unit according to an exemplary embodiment of the present disclosure, automatically finds out infected asymptomatic people by an intersection between contact pools of confirmed cases formed by different confirmed cases, backwardly tracks a source of pools which generate the tracing targets belonging to the intersection by an infection route tracking unit to find out an infection route of the confirmed case.

FIG. 3A illustrates a process of forming a confirmed case contact pool by the infected asymptomatic people searching unit 55a installed on the disease control authority terminal 55.

First, the infected asymptomatic people searching unit 55a distributes the confirmed case traffic line information to the voice recognition terminals 17, the voice recognition terminals 17 confirm whether the confirmed case traffic line distributed from the infected asymptomatic people searching unit 55a matches that of the tracing target and reports the tracing targets whose traffic line matches to the infected asymptomatic people searching unit 55a, and the infected asymptomatic people searching unit 55a collects and stores the reports to form a first cycle confirmed case contact pool (Cycle 1).

Further, the infected asymptomatic people searching unit 55a distributes the first cycle confirmed case contact pool to the voice recognition terminals 17 again, the voice recognition terminals 17 confirm whether the traffic line of the distributed first cycle confirmed case contact pool matches the traffic line of the tracing target and reports the matched tracing targets to the infected asymptomatic people searching unit 55a, and the infected asymptomatic people searching unit 55a collects and stores the reports to form a second cycle confirmed case contact pool (Cycle 2). When this process is repeated N times, N-th cycle confirmed case contact pool (Cycle N) may be created.

Hereinafter, the contact pool formed by n-th cycle confirmed case m is denoted by $P_{mn}$.

When this pool notation is used, a contact pool of a first cycle confirmed case 1 is denoted by $P_{11}$ and a contact pool of a second cycle confirmed case 1 is denoted by $P_{12}$.

That is, when the traffic line information of the confirmed case 1 is distributed to the voice recognition terminals 17 by the infected asymptomatic people searching unit 55a, the voice recognition terminals 17 report the tracing targets having the traffic line matching the traffic line of the confirmed case 1 to the infected asymptomatic people searching unit 55a, and the infected asymptomatic people searching unit 55a collects and stores the reports to form the confirmed case pool $P_{11}$.

Further, the $P_{11}$ traffic line information is re-distributed to the voice recognition terminals 17 and the voice recognition terminals 17 report the tracing targets having the traffic line matching the traffic line of the distributed $P_{11}$ to the infected asymptomatic people searching unit 55a, and the infected asymptomatic people searching unit 55a collects and stores the reports to form the confirmed case pool $P_{12}$.

For example, when M confirmed cases occur, a total "confirmed case 1 contact pool" may be generated by the confirmed case 1 as a union of pools consisting of the first cycle confirmed case 1 contact pool $P_{11}$, the second cycle confirmed case 1 contact pool $P_{12}$, . . . , and the N-th cycle confirmed case 1 contact pool $P_{1N}$.

Similarly, an entire "confirmed case 2 contact pool" may be generated by the confirmed case 2 as a union of pools consisting of a first cycle confirmed case 2 contact pool $P_{21}$, a second cycle confirmed case 2 contact pool $P_{22}$, . . . , and an N-th cycle confirmed case 2 contact pool $P_{2N}$.

Accordingly, when M confirmed case occurs, the confirmed case pools formed by performing up to the N cycle using the pool notation may be represented as follows.

$$\text{Confirmed case 1 contact pool} = \{P_{11}, P_{12}, \ldots, P_{1(N-1)}, P_{1N}\}$$
$$\text{Confirmed case 2 contact pool} = \{P_{21}, P_{22}, \ldots, P_{2(N-1)}, P_{2N}\}$$
$$\vdots$$
$$\text{Confirmed case M contact pool} = \{P_{M1}, P_{M2}, \ldots, P_{M(N-1)}, P_{MN}\}$$

The infected asymptomatic people searching unit 55a prefers to distribute the infection time range together to obtain the confirmed case contact pool. In other words, the infected asymptomatic people searching unit 55a may interlink and distribute the confirmed case contact pool and the infection time range to the voice recognition terminal 17.

For example, the infected asymptomatic people searching unit 55a distributes the infection time range to the voice recognition terminal 17 together with the confirmed case traffic line information in order to obtain the first cycle confirmed case contact pool. That is, the voice recognition terminals 17 report only the tracing targets having matching traffic lines to the infected asymptomatic people searching unit 55a within the infection time range while confirming whether the confirmed case traffic line distributed from the infected asymptomatic people searching unit 55a matches the traffic line of the tracing target.

Further, the infected asymptomatic people searching unit 55a distributes the infection time range to the voice recognition terminal 17 together with the first cycle confirmed case contact pool in order to obtain the second cycle confirmed case contact pool. That is, the voice recognition terminals 17 report only the tracing targets having matching traffic lines to the infected asymptomatic people searching unit 55a within the infection time range while confirming whether the first cycle confirmed case contact pool distributed from the infected asymptomatic people searching unit 55a matches the traffic line of the tracing target.

Desirably, the infection time range is preferably set to two weeks for each tracing target in the pool.

Figure 3B:
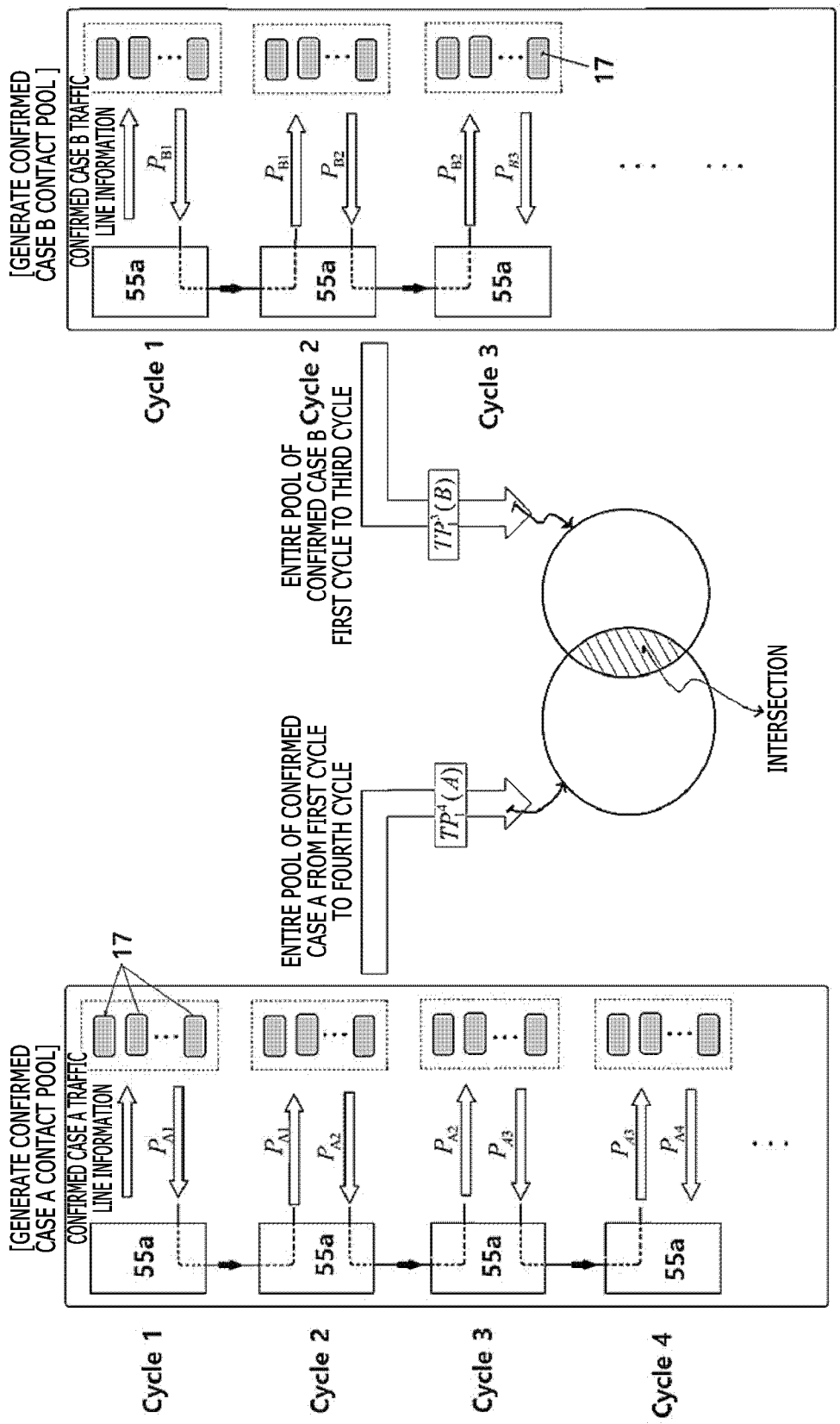

FIG. 3B illustrates a process of finding an intersection between the confirmed case contact pools generated by different confirmed cases, for example, a confirmed case A and a confirmed case B.

People belonging to the intersection stay in the same space at the same time so that it means that the traffic lines match.

Here, the entire confirmed case contact pools by the confirmed case A and the confirmed case B performed from cycle n1 to cycle n2 are denoted by $TP_{a1}^{a2}(A)$ and $TP_{n1}^{n2}(B)$, respectively.

$$TP_{a1}{}^{a2}(A)=\}P_{A1},P_{A2},\ldots,P_{A(N-1)},P_{AN}\}$$

$$TP_{n1}{}^{n2}(B)=\{P_{B1},P_{B2},\ldots,P_{B(N-1)},P_{BN}\}$$

The example of FIG. 3B(1) shows that there is no intersection between the first cycle confirmed case A contact pool $TP_1{}^1(A)$ by the confirmed case A and the first cycle confirmed case B contact pool $TP_1{}^1(B)$ by the confirmed case B.

Further, the example of FIG. 3B(2) shows that there is no intersection between the entire confirmed case contact pool $TP_1{}^3(A)$ by the confirmed case A performed from cycle 1 to cycle 3 and the entire confirmed case contact pool $TP_1{}^2(A)$ by the confirmed case B performed from cycle 1 to cycle 2.

However, the example of FIG. 3B(3) shows that there is an intersection between the entire confirmed case contact pool $TP_1{}^4(A)$ generated by the confirmed case A performed from cycle 1 to cycle 4 and the entire confirmed case contact pool $TP_1{}^3(B)$ generated by the confirmed case B performed from cycle 1 to cycle 3. The intersection provides information about the infection route by the infected asymptomatic people which connects the confirmed case A and the confirmed case B.

FIG. 3B will be explained using the pool notation, as follows:

$$TP_1{}^1(A)=P_{A1}, TP_1{}^1(B)=P_{B1},$$

$$TP_1{}^3(A)=P_{A1}+P_{A2}+P_{A3}, TP_1{}^2(B)=P_{B1}+P_{B2},$$

$$TP_1{}^4(A)=P_{A1}+P_{A2}+P_{A3}+P_{A4}, TP_1{}^3(B)=P_{B1}+P_{B2}+P_{B3};$$
and $$TP_1{}^1(A)\cap TP_1{}^1(B)=\emptyset, TP_1{}^3(A)\cap TP_1{}^2(B)=\emptyset, TP_1{}^4(A)\cap TP_1{}^3(B)\neq\emptyset.$$

Here, $\phi$ refers to a null set.

Figure 3C:
Figure 3C:
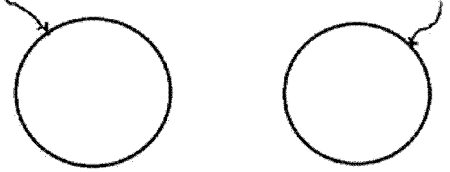
Figure 3C:
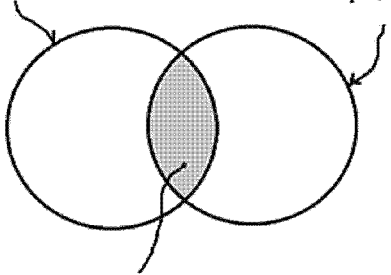

FIG. 3C shows a process of forming an entire confirmed case contact pool $TP_1{}^4(A)$ generated by the confirmed case A performed from cycle 1 to cycle 4 and a process of forming an entire confirmed case contact pool $TP_1{}^3(B)$ generated by the confirmed case B performed from cycle 1 to cycle 3.

The process of generating the confirmed case A contact pool will be explained. First, the infected asymptomatic people searching unit 55a distributes confirmed case A traffic line information to the voice recognition terminals 17, the voice recognition terminals 17 confirm whether the traffic line of the confirmed case A provided from the infected asymptomatic people searching unit 55a matches that of the tracing target and report the tracing targets whose traffic line matches to the infected asymptomatic people searching unit 55a, and the infected asymptomatic people searching unit 55a collects and stores the reports to form a first cycle (cycle 1) confirmed case A contact pool $P_{A1}$.

In a subsequent step, the infected asymptomatic people searching unit 55a distributes the cycle 1 confirmed case A contact pool $P_{A1}$ to the voice recognition terminals 17 again, the voice recognition terminals 17 confirm whether the traffic line of the distributed $P_{A1}$ (cycle 1 confirmed case contact pool) matches the traffic line of the tracing target and report the matched tracing targets to the infected asymptomatic people searching unit 55a, and the infected asymptomatic people searching unit 55a collects and stores the reports to form a cycle 2 confirmed case A contact pool $P_{A2}$. When this process is repeated to cycle 4, a cycle 4 confirmed case A contact pool $P_{A4}$ can be obtained.

This case may be expressed by $$TP_1^4(A)=\sum_{i=0}^{4}P_{Ai}.$$

Similarly, the entire confirmed case B contact pool performed from cycle 1 to cycle 3 may be expressed by $$TP_1^3(B)=\sum_{i=0}^{3}P_{Bi}.$$

Further, the exemplary embodiment of FIG. 3C shows that an intersection which provides information about an infection connection link between the confirmed case A and the conformed case B is formed between $TP_1{}^4(A)$ and $TP_1{}^3(B)$. The intersection provides information about the infection route by the infected asymptomatic people which connects the confirmed case A and the confirmed case B.

FIG. 3C can be explained using the pool notation as follows:

$$TP_1{}^4(A)=P_{A1}+P_{A2}+P_{A3}+P_{A4}, TP_1{}^3(B)=P_{B1}+P_{B2}+P_{B3} \text{ and } TP_1{}^4(A)\cap TP_1{}^3(B)\neq\emptyset.$$

FIG. 3C is an exemplary embodiment that a first intersection between the contact pool generated by the confirmed case A and the contact pool generated by the confirmed case B is generated in $TP_1{}^4(A)$ and $TP_1{}^3(B)$.

That is, the first intersection is generated between the cycle 4 confirmed case A contact pool and the cycle 3 confirmed case B contact pool and a cycle at which the first intersection is generated is denoted by $(i_o,j_o)$ Here, $i_o$ is a cycle of the confirmed case A contact pool at the time when the first intersection is generated and $j_o$ is a cycle of the confirmed case B contact pool at the time when the first intersection is generated.

Therefore, the first intersection is generated in $TP_1{}^4(A)$ and $TP_1{}^3(B)$ so that $(i_o, j_o)=(4, 3)$.

An exemplary embodiment of an artificial intelligence algorithm program (an expert system) which is mounted on the infected asymptomatic people searching unit 55a to found $(i_o,j_o)$ will be schematically explained as follows:

```
Intersection....Index = [ ]
  for i = 1: max(i)
        for j = 1:: max(j)
              if TP₁ⁱ(A) ∩TP₁ʲ(B) ≠ ϕ
                    include (i,j) in the set of Intersection_Index
              end
        end
  end,
```

Here, (i, j) included in the set Intersection_Index refers to a cycle of the contact pools whose intersection is not a null set. That is, it is a set of the cycles (i, j) which generate the intersection. In other words, Here, i in the Intersection_Index (i, j) is a cycle of the confirmed case A contact pool at the time when the intersection is generated and j in the Intersection_Index (i, j) is a cycle of the confirmed case B contact pool at the time when the intersection is generated.

While executing for loop, values of i and j increase so that the size of the acquired confirmed case A pool and the size of the acquired confirmed case B are also gradually increased. The pool sizes of the confirmed case A pool $TP_1{}^1(A)$ and the confirmed case B pool $TP_1{}^1(B)$ need to be increased until the intersection between the confirmed case A pool and the conformed case B pool is found, but an upper limit needs to be set.

In the present disclosure, the upper limit is defined as variables max(i) and max(j). Here, max(i) is a maximum cycle for generating the confirmed case A contact pool and max(j) is a maximum cycle for generating the confirmed case B contact pool.

$(i_o, j_o)$ may be determined to be selected as one of (i, j) values included in the set Intersection_Index from the above-described algorithm program. $(i_o, j_o)$ may be selected by a method such as the following examples.

The infected asymptomatic people searching unit 55a may apply at least one method selected from the following examples to find out $(i_o, j_o)$ $$(i_o, j_o) = \min_{i,j} \text{size}[TP_1^i(A) \cap TP_1^j(B) | \forall (i, j) \in \text{Intersection\_Index}]$$

or $$(i_o, j_o) = \min_{i,j} [(i + j) | \forall (i, j) \in \text{Intersection\_Index}]$$

or $$(i_o, j_o) = \min_{i,j} [\text{absolute}(i - j) | \forall (i, j) \in \text{Intersection\_Index}]$$

or $$(i_o, j_o) = \min_{i,j} [\min(i, j) | \forall (i, j) \in \text{Intersection\_Index}]$$

or $$(i_o, j_o) = \min_{i,j} [\max(i, j) | \forall (i, j) \in \text{Intersection\_Index}].$$

Here, $\forall (i,j) \in$ Intersection_Index refers to all (I, j) included in the set Intersection_Index.

Further, min(i,j) refers to a minimum value between i and j, max(i,j) refers to a maximum value between i and j, absolute (i-j) refers to an absolute value of (i-j), and size $[TP_1^i(A) \cap TP_1^i(B)]$ refers to a size of the intersection formed between $TP_1^i$ (A) and $TP_1^i$(B).

Accordingly, $$(i_o, j_o) = \min_{i,j} \text{size}[TP_1^i(A) \cap TP_1^j(B) | \forall (i, j) \in \text{Intersection\_Index}]$$

means that among all (i,j) included in Intersection_Index, (i,j) which makes the size of the intersection formed between $TP_1^i$ (A) and $TP_1^i$(B) shortest is selected as $(i_o, j_o)$.

Further, $$(i_o, j_o) = \min_{i,j} [(i + j) | \forall (i, j) \in \text{Intersection\_Index}]$$

means that among all (i,j) included in Intersection_Index, (i,j) which makes (i+j) shortest is selected as $(i_o, j_o)$.

Similarly, $$(i_o, j_o) = \min_{i,j} [\min(i, j) | \forall (i, j) \in \text{Intersection\_Index}]$$

means that among all (i,j) included in Intersection_Index, (i, j) when a minimum value between i and j is selected and the selected minimum value becomes minimum is selected as $(i_o, j_o)$.

Here, max(i) is determined by a maximum allowable time to go back to the past time to find an origin of an initial infection from the time when the confirmed case A occurs.

Similarly, max(j) is determined by a maximum allowable time to go back to the past time to find an origin of an infection from the time when the confirmed case B occurs.

Initial values of the parameters max(i) and max(j) prefer to be determined by times of two weeks to three weeks.

The values of the parameters max(i) and max(j) are desirably determined by a disease control policy of the disease control authority, but preferably increased in proportional to the increase of the confirmed cases.

According to another aspect, the values of the parameters max(i) and max(j) are preferably increased in proportional to the increase of the confirmed cases whose infection routes are not known.

According to another aspect, the values of the parameters max(i) and max(j) are preferably increased in proportional to a basic reproduction number (basic reproductive ratio) R0 (R naught) indicating a rate at which the infectious disease is propagated.

The infected asymptomatic people searching unit 55a may calculate the intersection between the confirmed case A contact pool and the confirmed case B contact pool by a cycle $(i_o, j_o)$ at which the first intersection found by the artificial intelligence algorithm program is generated, as follows, and this intersection provides information about the infection route by the infected asymptomatic people.

$$\text{Intersection} = TP^{io}_1(A) \cdot TP^{io}_1(B)$$

The exemplary embodiment illustrates an example that finds out infected asymptomatic people by the intersection between the contact pool generated by the confirmed case A and the contact pool generated by the confirmed case B, that is, two confirmed cases. However, when the same principle is expanded to the case that a plurality of confirmed cases occurs, the exemplary embodiment can be applied to a plurality of confirmed cases by the computer program. Actually, as the number of confirmed cases increases, the probability that the intersection becomes the origin of infected asymptomatic people increases even more.

Figure 3D:
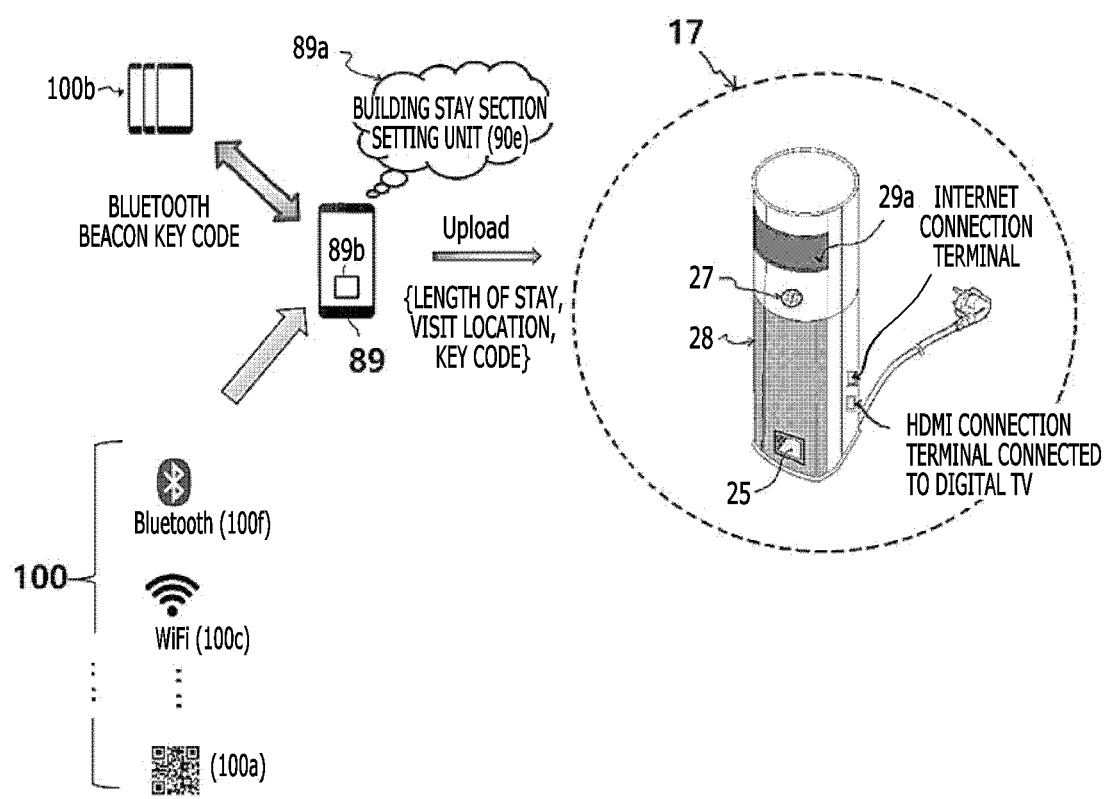

FIG. 3D illustrates an exemplary embodiment that finds an infection route and an infection source by the infection route tracking unit when a first intersection between the contact pool generated by the confirmed case A and the contact pool generated by the confirmed case B is generated between $TP^4_1(A)$ and $TP^3_1(B)$. That is, the first intersection is generated between the entire confirmed case A contact pool $TP^4_1(A)$ from cycle 1 to cycle 4 and the entire confirmed case B contact pool $TP^3_1(B)$ from cycle 1 to cycle 3 and this case corresponds to $(i_o, j_o) = (4, 3)$.

In FIG. 3D, the symbol • indicates a component of the confirmed case A contact pool which is tracing targets who have a contact with the confirmed case A before the positive is confirmed and the symbol O indicates a component of the confirmed case B contact pool which is tracing targets who have a contact with the confirmed case B before the positive is confirmed.

The component of the confirmed case contact pool is configured by tracing targets which have a contact with the confirmed case before the positive is confirmed and includes personal information, visit locations, and length of stay information of the tracing targets.

Another aspect of the component of the confirmed case contact pool is configured by tracing targets who have a contact with the confirmed case in a short distance by the Bluetooth beacon of the cellular phone before the confirmed case is confirmed as positive and includes Key code information of the Bluetooth beacons of the confirmed case and the tracing targets.

Further, still another aspect of the component of the confirmed case contact pool is configured by tracing targets who have a contact with the confirmed case before the confirmed case is confirmed as positive and includes location information (visit location and a length of stay) of the cellular phone 89 of the tracing targets provided from the location information providing unit 100 and the personal information of the tracing target.

The infection route tracking unit may find out the infection routes 500A and 500B by backwardly tracking in a time axis direction on the confirmed case A contact pool and the confirmed case B contact pool with the intersection obtained by a comparing process between the confirmed case contact pools. The reference numeral 500A is an infection route obtained by the process of backwardly tracking in the time axis on the confirmed case A contact pool starting from the intersection and the reference numeral 500B is an infection route obtained by the process of backwardly tracking in the time axis on the confirmed case B contact pool starting from the intersection. All the people (components) on the infection routes become the subjects of self-quarantine so that the disease pandemic can be suppressed early. Even though FIG. 3D illustrates an example that finds an intersection using the contact pool of two confirmed cases (confirmed case A and confirmed case B), in fact, as the number of confirmed cases is increased, the likelihood that the intersection becomes the origin of the infected asymptomatic people increases even more.

Figure 4A:
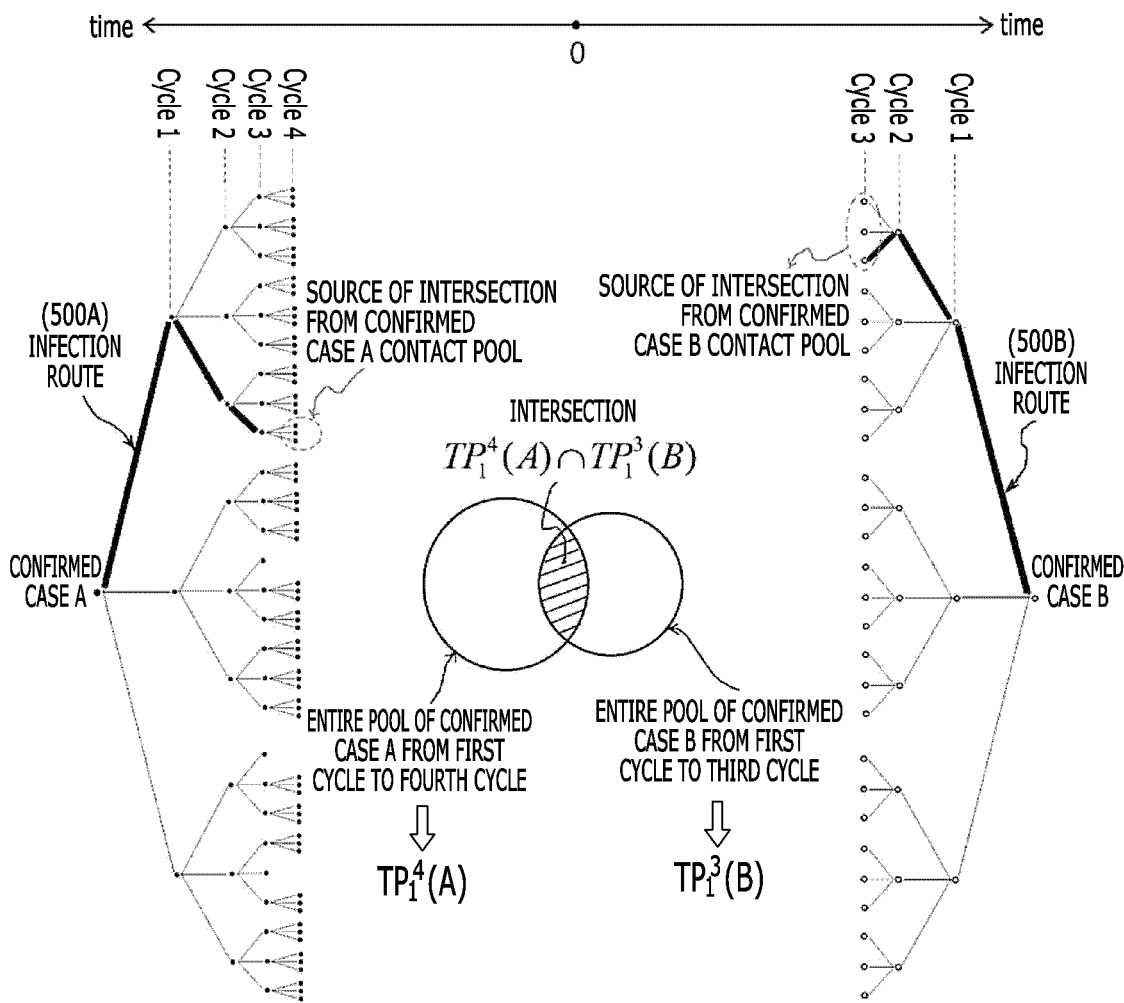
FIG. 4A is a view schematically illustrating an exemplary embodiment that stores Key codes provided from cellular phones of short-distance contacts by a Bluetooth beacon in a resident memory on a cellular phone of a tracing target and uploads the Key codes stored in the resident memory to a storage space in a voice recognition terminal by wireless connection with a voice recognition terminal of the cellular phone of the tracing target.

FIG. 4A is a view schematically illustrating an exemplary embodiment that stores Key codes provided from cellular phones 100*b* of short-distance contacts by a Bluetooth beacon in a resident memory 89*b* on a cellular phone 89 of a tracing target and uploads the Key codes stored in the resident memory 89*b* to a storage space (for example, a tracing target traffic line information memory) in a voice recognition terminal 17 by wireless connection with the voice recognition terminal 17 by the cellular phone 89 of the tracing target.

The Bluetooth beacon may be replaced with an ultrasonic beacon or an infrared beacon. The infrared beacon prefers to use an infrared signal transmitted from a cellular phone including an IR LED. As the infrared ray, a near-infrared ray which is transmitted to the outside by passing through the clothing even though the infrared beacon is in a pocket is preferred.

However, the key code does not include information about the visit location of the tracing target so that there is a problem in that the location information of the tracing target cannot be found out only by the key code. In order to solve this problem, according to the exemplary embodiment, the traffic line tracing management application 89*a* installed on the cellular phone 89 of the tracing target may include a building stay section setting unit 90*e*. Preferably, the visit location and the length of stay information are obtained by the building stay section setting unit 90*e* and is synchronized with the Key code to be stored on the resident memory 89*b* on the cellular phone 89 of the tracing target as location information.

The building stay section setting unit 90*e* tracks and checks location information or location ID (Bluetooth transmitter ID, Wi-Fi ID, or QR code) information provided from the location information providing unit 100 to calculate a length of stay indicating how long the cellular phone 89 of the tracing target stays in the building (visit location).

For example, referring to FIG. 4A, the building stay section setting unit 90*e* tracks and checks location ID (Bluetooth transmitter ID, Wi-Fi ID, or QR code) information provided from the Bluetooth transmitter 100*f*, a QR code 100*a*, or a Wi-Fi 100*c* installed in the building to calculate a length of stay indicating how long the cellular phone 89 of the tracing target stays in the building (visit location).

Another aspect of the building stay section setting unit 90*e* may know when the cellular phone 89 of the tracing target enters the building (visit location) and leave the building, by the combination of the location ID information and location information of a GPS coordinate or a base station.

For example, when the people enter the building through the QR code registration procedure, but leave the building without performing the QR code registration procedure, the building stay section setting unit 90*e* is useful to find out the length of stay. For example, the building stay section setting unit 90*e* stores the GPS coordinate at the time of entering with the QR code registration procedure and when a current GPS coordinate is out of the GPS coordinate at the time of entering by a predetermined range or more, determines that the people leave to calculate the length of stay in the building (the visit location).

Further, the confirmed case contact pool according to the exemplary embodiment of the present disclosure may be formed to include length of stay and visit location information as well as the key code information of the cellular phones which share the Key code by the Bluetooth beacon.

The cellular phone 89 of the tracing target reads the key codes acquired from the cellular phone 100*b* of short-distance contacts stored on the resident memory 89*b* which are acquired during the building stay period, by means of wireless communication connection with the voice recognition terminal 17, at the stay ending time of the building calculated by the building stay section setting unit 90*e* to upload the key codes in the storage space (for example, the tracing target traffic line information memory) of the voice recognition terminal 17. Further, the building stay section information (length of stay and visit location) eis read together with the key codes to be uploaded in the storage space of the voice recognition terminal 17.

The traffic line tracing management application 89*a* prefers to delete the Key code and the location information remaining on the resident memory 89*b* after uploading the information in the storage space of the voice recognition terminal 17.

Figure 4B:
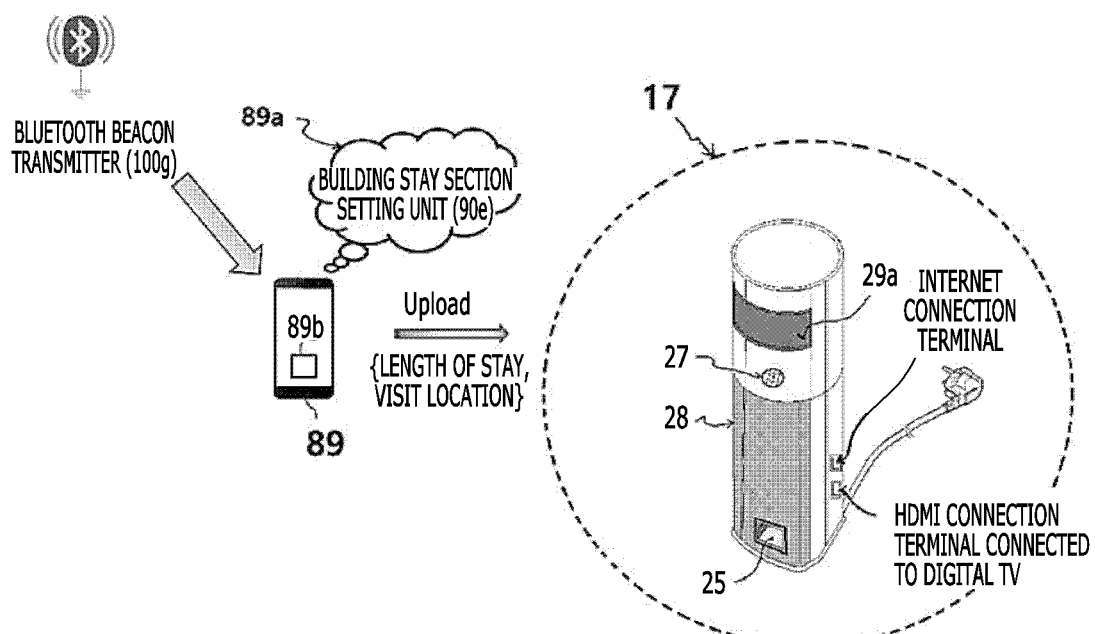
FIG. 4B is a view schematically illustrating an exemplary embodiment that stores visit location information and length-of-stay information in a resident memory on a cellular phone of a tracing target by communication connection between a Bluetooth beacon installed in one region in a visit location and a cellular phone of the tracing target staying in the visit location, and uploads building stay section information (visit location and length-of-stay information) stored in the resident memory to a storage space in a voice recognition terminal by wireless connection with a voice recognition terminal of the cellular phone of the tracing target.

FIG. 4B is a view schematically illustrating an exemplary embodiment that stores visit location and length-of-stay information in a resident memory 89*b* on a cellular phone 89 of a tracing target by Bluetooth communication connection between a Bluetooth beacon 100*g* installed in one region in a visit location of the tracing target and a cellular phone 89 of the tracing target staying in the visit location, and uploads the visit location and the length-of-stay information stored in the resident memory 89*b* in the storage space (for example, the tracing target traffic line information memory) in a voice recognition terminal 17 by means of connection with the voice recognition terminal 17 by the cellular phone 89 of the tracing target.

The Bluetooth beacon transmitter 100*g* is a device which is one of short-distance wireless sensors and recognizes the location of a smartphone user to exchange data. The Bluetooth beacon transmits a received signal strength indicator (RSSI) value so that a distance between the Bluetooth beacon transmitter 100*g* and the cellular phone 89 is found using the output signal strength and a signal intensity of the beacon which have been already known and a length of stay indicating how long the people stay in the visit location may be calculated.

The Bluetooth beacon transmitter 100g prefers to emit an information packet including a universally unique identifier (UUID) to the outside to be received by a cellular phone 89 in a short distance (appropriately, within 10 m). The traffic line tracing management application 89a considers the received UUID information itself as visit location information to store the UUID information in the resident memory 89b or store visit location information obtained by converting the UUID information into a building address by a server in the resident memory 89b.

When a user who carries the cellular phone 89 of the tracing target enters in a signal area of the Bluetooth beacon, a transmitter of the Bluetooth beacon transmitter 100g provides UUID or visit location (building address) information to the traffic line tracing management application 89a. At this time, the traffic line tracing management application 89a stores the information in the resident memory 89b on the cellular phone 89 of the tracing target, together with the length of stay information.

In the exemplary embodiment of FIG. 4B, the traffic line tracing management application 89a installed on the cellular phone 89 of the tracing target may include the building stay section setting unit 90e and the visit location and the length of stay information acquired by the building stay section setting unit 90e is stored in the resident memory 89b on the cellular phone 89 of the tracing target.

The building stay section setting unit 90e tracks and checks the signal intensity of the RSSI emitted from the transmitter of the Bluetooth beacon 100g to calculate a length of stay indicating how long the cellular phone 89 of the tracing target stays in the building (visit location).

That is, the building stay section setting unit tracks and checks the UUID and the received signal strength indicator (RSSI) value provided from the Bluetooth beacon to calculate the length of stay and the visit location that the cellular phone of the tracing target stays in the building to store the information in the resident memory on the cellular phone of the tracing target.

Further, at the stay ending time of the building calculated by the building stay section setting unit, the building stay section setting unit reads cellular phone location information (length of stay and visit location) of the tracing target which is cumulatively stored in the resident memory of the cellular phone of the tracing target to upload the locating information to the tracing target traffic line information memory by means of the digital communication module.

Further, the voice recognition terminal 17 illustrated in FIGS. 4A and 4B includes a body temperature check diagnosis unit 26 which determines a temperature suspicious target on the basis of information collected from the tracing target and a fingerprint authentication unit 25 which checks whether a fingerprint input from a fingerprint sensor matches a previously registered fingerprint of the tracing target to perform identity authentication. Further, the body temperature check diagnosis unit 26 includes a non-contact temperature sensor 29a including a thermal imaging camera which detects a thermal radiation emitted from a body of the tracing target to provide a thermal image or an IR temperature sensor which detects an IR ray emitted from the body of the tracing target to measure a temperature and a body temperature determining unit which measures a temperature value of the patient from the non-contact temperature sensor 29a to determine the patent as an abnormal temperature suspicious target when the temperature is an abnormal body temperature.

The artificial intelligence-infected asymptomatic people movement-tracing apparatus according to the exemplary embodiment of the present disclosure may include a digital communication module 8 which is installed in one region of a residence of the tracing target and provides communication with the disease control authority terminal, provides wireless communication connection with the cellular phone of the tracing target, or provides short-distance communication (for example, Bluetooth or Wi-Fi) with the cellular phone of the tracing target. Further, the artificial intelligence-infected asymptomatic people movement-tracing apparatus is installed in the cellular phone 89 of the tracing target (not only resides as an application) and cumulatively stores the cellular phone location information of the tracing target provided from the plurality of location information providing units 100 in the resident memory on the cellular phone of the tracing target and may wirelessly transmit the cellular phone location information to the digital communication module as needed. Further, the artificial intelligence-infected asymptomatic people movement-tracing apparatus may include the traffic line tracing management application 89a which periodically wirelessly transmits the cellular phone location information which is cumulatively stored in the resident memory on the cellular phone 89 to the remote server 200. Further, the artificial intelligence-infected asymptomatic people movement-tracing apparatus may include a communication connection checking unit which resides (is installed) in the traffic line tracing management application (APP) and checks the Bluetooth or Wi-Fi communication connection between the digital communication module and the cellular phone or transmits cellular phone location information of the tracing target which is cumulatively stored in the resident memory 89b on the cellular phone 89 to the digital communication module whenever the tracing target leaves the residence and then re-enters the residence. Further, the artificial intelligence-infected asymptomatic people movement-tracing apparatus may include a tracing target traffic line information memory 20 which stores the traffic line history information of the cellular phone of the tracing target and a memory scheduler 19 which updates the cellular phone location information of the tracing target cumulatively stored in the resident memory of the cellular phone of the tracing target to the tracing target traffic line information memory 20 by means of the digital communication module 8. Further, the artificial intelligence-infected asymptomatic people movement-tracing apparatus may include a confirmed case traffic line information memory 21 which stores traffic line information of the confirmed case provided from the disease control authority terminal 55 by means of the digital communication module 8. Further, the artificial intelligence-infected asymptomatic people movement-tracing apparatus may include a traffic line matching determining unit 22 which compares the contents of the confirmed case traffic line information memory and the tracing target traffic line information memory to find out whether the traffic line of the tracing target matches the traffic line of the confirmed case. Further, in the case of outbreak of epidemic infection spread, the disease control authority terminal provides the traffic line information of the confirmed case to the confirmed case traffic line information memory 21 by means of the digital communication module 8 and the artificial intelligence-infected asymptomatic people movement-tracing apparatus may include a controller 30 that when the traffic line of the tracing target overlaps the traffic line of the confirmed case, drives the digital communication module 8 to select the tracing target as a subject of self-quarantine to automatically transmit information of the tracing target to the disease control authority terminal 55. Further, the artificial intelligence-infected asymptomatic people movement-tracing apparatus may include a control right handover unit which transfers the control right of the controller 30 to the disease control authority terminal.

Further, the artificial intelligence-infected asymptomatic people movement-tracing apparatus may form a confirmed case contact pools to collect and store tracing targets only having the traffic lines overlapping the traffic lines of the confirmed cases. At this time, the infected asymptomatic people searching unit automatically finds out infected asymptomatic people by finding the intersection between contact pools of different confirmed cases. Further, the artificial intelligence-infected asymptomatic people movement-tracing apparatus of the present disclosure includes an infection route tracking unit which temporally backwardly tracks the confirmed case contact pools with the found intersection to find out an infection source and an infection route from which the confirmed case is generated.

Further, the confirmed case traffic line information includes any one or more location information selected from a GPS coordinate on the traffic line of the cellular phone of the confirmed case, base station information to which the cellular phone of the confirmed case accesses, a visiting place QR code of the confirmed case, beacon Key codes of the cellular phone of the confirmed case, a Bluetooth transmitter ID collected by the cellular phone of the confirmed case, and Wi-Fi ID information to which the cellular phone of the confirmed case accesses and length of stay information on the traffic line of the confirmed case which is synchronized according to the location information. A start time and an end time of the length of stay in the building on the traffic line of the confirmed case are preferably determined after the epidemiological survey of the confirmed case performed by the disease control authority.

Further, the traffic line history information of the cellular phone of the tracing target includes any one or more location information selected from a GPS coordinate on the traffic line of the cellular phone of the tracing target, base station information to which the cellular phone of the tracing target accesses, a visiting place QR code of the tracing target, Key codes collected by the cellular phone of the tracing target, a Bluetooth transmitter ID collected by the cellular phone of the tracing target, and Wi-Fi ID information to which the cellular phone of the tracing target accesses and length of stay (staying hour) information which is synchronized according to the location information.

Further, the traffic line tracing management application 89a further includes a stay valid filter which extracts (selects) only the location information where the tracing target stays in the same location (the same location and the same building) for a predetermined time or longer, among location information of the cellular phone provided from the plurality of location information providing units as valid location information to cumulatively store the valid location information in the resident memory of the cellular phone of the tracing target.

Further, the plurality of location information providing units 100 may include at least one of a GPS (global positioning system) which provides location data of the cellular phone using a satellite, a Bluetooth transmitter or a Bluetooth beacon which provides a unique ID of Bluetooth to the cellular phone, cellular phones of short-distance contacts which share Key codes by the Bluetooth beacon, an access point (AP) of a wireless LAN which provides a Wi-Fi ID to the cellular phone, a black and white grid pattern which provides a QR code of the visit place to the cellular phone, and a base station which provides mobile communication location information accessing the cellular phone.

Further, according to another aspect of the stay valid filter, when the same Key code is generated a predetermined number of times or more per hour, the stay valid filter selects the Key codes which are generated a predetermined number of times or more as valid key code information to cumulatively store the Key codes in the resident memory on the cellular phone.

Further, the traffic line tracing management application 89a includes a self-quarantine confirming unit and when the controller 30 or the disease control authority terminal 55 provides notification information (for example, text information) informing to be confirmed as a subject of self-quarantine to the cellular phone of the tracing target who is confirmed as a subject of self-quarantine and the tracing target confirms the notification information displayed on the cellular phone by means of the fingerprint authentication procedure, the self-quarantine confirming unit confirms the tracing target as a subject of self-quarantine.

Further, the plurality of location information providing units and the cellular phone location information may include a building address which is expressed to be combined with building information provided by geographic information system (GIS) building-integrated information.

According to the exemplary embodiment of the present disclosure, the artificial intelligence-infected asymptomatic people movement-tracing apparatus may include a voice recognition terminal 17 which is installed in one region in the residence of the tracing target and not only is connected to the digital TV (or smart mirror) which provides various contents by high-speed Internet connection, but also includes a voice recognition unit 27a and a voice reproducing unit 28a to control the digital TV (or the smart mirror) by voice instruction collected by the microphone 27 and provide a voice feedback service by the speaker. The voice recognition terminal 17 may include a digital communication module 8 which provides communication with the disease control authority terminal, wireless communication connection with the cellular phone of the tracing target, or provides short-distance communication connection with a cellular phone of the tracing target. Further, the voice recognition terminal 17 may include a tracing target traffic line information memory 20 which stores traffic line history information of the tracing target cellular phone and a memory scheduler which reads and uploads the cellular phone location information of the tracing target cumulatively stored in the resident memory on the cellular phone of the tracing target to the tracing target traffic line information memory 20 by the connection with the digital communication module 8 or drives the digital communication module 8 to read the traffic line history information of the tracing target from the remote server 200 at every predetermined time to upload the traffic line history information of the tracing target in the tracing target traffic line information memory 20 and delete the traffic line history information of the tracing target stored in the remote server after completely uploading. Further, the voice recognition terminal 17 may include a confirmed case traffic line information memory 21 which stores traffic line information of the confirmed case provided from the disease control authority terminal by means of the digital communication module 8, a traffic line matching determining unit 22 which finds out whether there is a route in which the traffic line of the tracing target overlaps the traffic line of the confirmed case by comparing the confirmed case traffic line information and the tracing target traffic line information, the controller 30 which when there is a route in which the traffic line of the tracing target overlaps the traffic line of the confirmed case, selects the tracing target as a subject of self-quarantine and drives the digital communication module 8 to transmit the information of the selected subject of self-quarantine to the disease control authority terminal 55, and a control right handover unit which transfers the control right of the controller to the disease control authority terminal 55. The cellular phone 89 of the tracing target cumulatively stores location information of the cellular phone provided from a plurality of location information providing units 100 in a resident memory on the cellular phone, or wirelessly transmits and uploads location information of the cellular phone to the voice recognition terminal 17 by means of the connection with the digital communication module at every predetermined time or periodically wirelessly transmits cellular phone location information cumulatively stored in the resident memory to the remote server 200.

Further, the voice recognition terminal 17 includes a medical data receiver 12 which receives medical data measured from a plurality of medical devices by means of short-distance communication connection between the digital communication module 8 and the medical devices and an artificial intelligence neural network 16 which is deep-learning trained in advance by the medical data for learning. The deep learning-trained artificial intelligence neural network 16 analyzes the medical data received by the medical data receiver 12 to automatically determine whether the patient has a disease and a risk of the disease.

Further, the cellular phone 89 of the tracing target includes a building stay section setting unit and the building stay section setting unit tracks and checks location information provided from the location information providing unit to calculate a length of stay indicating how long the cellular phone of the tracing target stays in the building. The cellular phone of the tracing target reads the key codes acquired from the cellular phone of short-distance contacts during the building stay period, by means of wireless communication connection with the voice recognition terminal 17, at the stay ending time of the building calculated by the building stay section setting unit to upload the key codes in the tracing target traffic line information memory of the voice recognition terminal 17.

Further, the voice recognition terminal 17 may be integrated into the digital TV (or the smart mirror).

Figure 5:
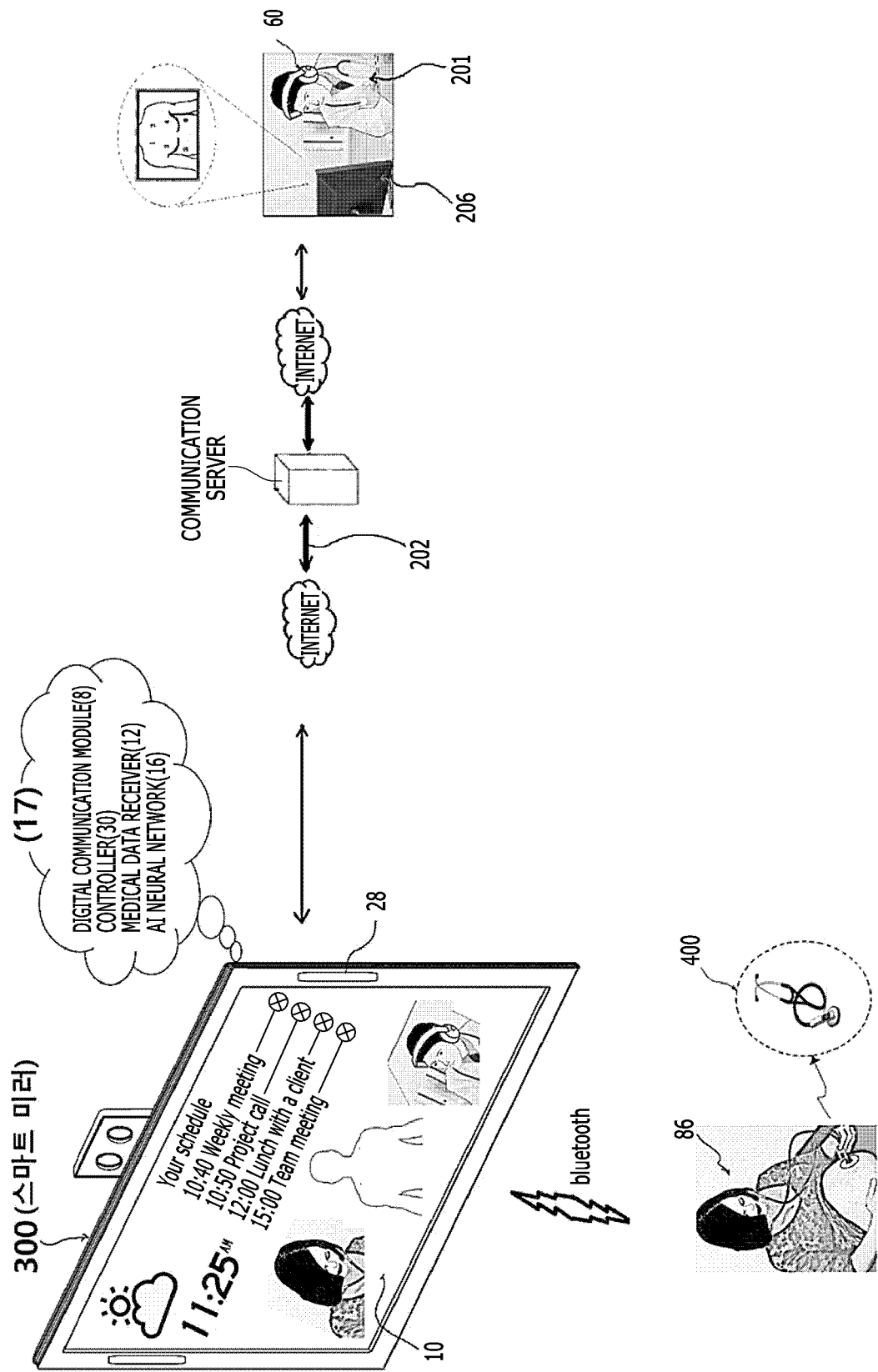
FIG. 5 is a view schematically illustrating an exemplary embodiment which performs remote medical diagnosis to allow a doctor to remotely check a health condition of a fetus using a stethoscope which provides Bluetooth connection with a digital TV (or a smart mirror).

According to an exemplary embodiment of the present disclosure, an infected asymptomatic people movement-tracing method (hereinafter, referred to as this method) performed by the artificial intelligence-infected asymptomatic movement-tracing apparatus may include a step of registering Bluetooth or Wi-Fi connection between a cellular phone of the tracing target and a digital communication module. Further, this method may include a step of allowing the terminal of the disease control authority to request a control right of the infected asymptomatic people movement-tracing apparatus to the cellular phone of the tracing target. Further, this method may include a step of allowing the tracing target to transfer the control right of the infected asymptomatic people movement-tracing apparatus to the disease control authority on the basis of handover information generated by a predetermined authentication procedure by means of the computer application or a mobile application. Further, this method may include a step of transmitting traffic line information of the tracing target stored in the resident memory on the cellular phone of the tracing target to the digital communication module when it is determined that the tracing target leaves and re-enters the residence by the communication connection checking unit. Further, this method may include a step of allowing the disease control authority terminal to transmit the confirmed case traffic line information to the digital communication module when the confirmed case is generated. Further, this method may include a step of reporting the tracing target as a subject of self-quarantine to the disease control authority terminal when the traffic line of the tracing target and the traffic line of the confirmed case overlap and a step of issuing a notice informing to be confirmed as a subject of self-quarantine to the cellular phone of the tracing target and allowing the tracing target to open and read the notice by a fingerprint authentication procedure provided to the cellular phone to be confirmed as a subject of self-quarantine. Further, this method may include a step of automatically finding out infected asymptomatic people corresponding to the infection source by an intersection between the confirmed case contact pools. Further, this method may include a step of finding out an infection route by backwardly tracking infected asymptomatic people corresponding to an infection source included in the intersection from the confirmed case contact pool and additionally confirming and notifying that the tracing target on the infection route as a subject of self-quarantine. FIG. 5 is a view schematically illustrating an exemplary embodiment which performs remote medical diagnosis to allow a doctor to remotely check a health condition of a fetus using a stethoscope 400 which provides Bluetooth connection with a digital TV 300. For example, FIG. 5 is an exemplary embodiment that a doctor 201 performs remote medical diagnosis by utilizing a digital TV 300 connected with a stethoscope 400 by Bluetooth to check health conditions of a pregnant woman 86 and a fetus. In the exemplary embodiment, the digital TV 300 may be replaced with a smart mirror.

The voice recognition terminal 17 of FIG. 2 which is integrately embedded in the digital TV 300 may include a digital communication module 8 which provides a network 202 and Wi-Fi communication connection or short-distance communication connection (Bluetooth connection) with a stethoscope 400 to allow remote medical diagnosis with a doctor 201, a medical data receiver 12 which receives medical data measured from the pregnant woman by the stethoscope 400, an artificial intelligence neural network 16 which is deep-learning trained in advance by medical data for learning, and a controller 30 which controls the digital communication module 8, a speaker 28, and a screen display unit 10 to perform remote medical diagnosis with the doctor 201 and the pregnant woman 86.

The digital TV 300 provides visual information helping the remote medical diagnosis during the remote medical diagnosis to the screen display unit 10 to share the screen between the pregnant woman 86 and the doctor 201. Further, the digital TV 300 may provide guidelines for health management, a remote medical diagnosis method, and a guideline for how to use the stethoscope to the pregnant woman through the speaker 28. Further, the deep learning-trained artificial intelligence neural network 16 analyzes the medical data from the stethoscope 400 received by the medical data receiver 12 to automatically determine whether the pregnant woman and the fetus have diseases and a risk of the disease.

Further, the controller 30 may drive the digital communication module 8 so as to coincide information displayed on the screen display unit 10 and information watched by the doctor on the monitor 206.

In this case, the doctor shares the real-time information with the pregnant woman 86 by means of the monitor 206 so that the doctor directly instructs the pregnant woman 86 how to use the stethoscope 400 using a voice by means of the communication network 202 so that the fetus health diagnosis of the pregnant woman can be helped as if there is the doctor 201 next to the pregnant woman 86.

The reference numeral 60 indicates that the doctor can remotely hear the heartbeat sound of the fetus heard from the stethoscope 400 with headphones.

Hereinafter, an operation flow of the present disclosure will be described in brief based on the above-detailed description.

Even though not illustrated in the drawings, the artificial intelligence-infected asymptomatic people movement-tracing method may be performed by the above-described infected asymptomatic people movement-tracing apparatus, the voice recognition terminal 17, and a digital TV or a smart mirror 300 in which the voice recognition terminal 17 is embedded. Accordingly, even though omitted below, the description of the infected asymptomatic people movement-tracing apparatus, the voice recognition terminal 17, and the digital TV or the smart mirror 300 can be applied to the description of the infected asymptomatic people movement-tracing method in the same manner. Hereinafter, for the convenience of description, it will be described that the method is performed by the infected asymptomatic people movement-tracing apparatus (not illustrated).

In step S101, the infected asymptomatic people movement-tracing apparatus (not illustrated) may register Bluetooth or Wi-Fi connection between the cellular phone of the tracing target and the digital communication module.

In step S102, the infected asymptomatic people movement-tracing apparatus (not illustrated) may allow a terminal of the disease control authority to request the tracing target a control right of the movement-tracing apparatus.

In step S103, the infected asymptomatic people movement-tracing apparatus (not illustrated) may allow the tracing target to transfer the control right of the infected asymptomatic people movement-tracing apparatus or the traffic line tracing management application to the disease control authority on the basis of handover information generated by a predetermined authentication procedure by means of a computer application of the tracing target or a mobile application (app) installed in the cellular phone of the tracing target.

In step S104, the infected asymptomatic people movement-tracing apparatus (not illustrated) may allow the communication connection checking unit to transmit the traffic line (location history information of the cellular phone) of the tracing target stored in the resident memory on the cellular phone of the tracing target to the digital communication module when it is determined that the tracing target leaves the residence and then re-enters.

In step S105, the infected asymptomatic people movement-tracing apparatus (not illustrated) may allow the disease control authority terminal to transmit the confirmed case traffic line information through the digital communication module when the confirmed case is generated.

In step S106, the infected asymptomatic people movement-tracing apparatus (not illustrated) may report (provide) the tracing target as a subject of self-quarantine to the disease control authority terminal when the traffic line of the tracing target overlaps the traffic line of the confirmed case.

In step S107, the disease control authority terminal 55 may transmit a notice informing that the tracing target is confirmed as the subject of self-quarantine to the cellular phone of the subject of self-quarantine and the subject of self-quarantine opens the notice by the fingerprint authentication procedure on the cellular phone to confirm the subject of self-quarantine.

In step S108, the infected asymptomatic people movement-tracing apparatus (not illustrated) may allow the infected asymptomatic people searching unit 55a to generate confirmed case contact pools, when an intersection between the generated confirmed case contact pools occurs, backwardly track origins of the confirmed case contact pools which generate the intersection by the infection route tracking unit to find out an infection route and additionally designate the people on the infection route as subjects of self-quarantine.

In the meantime, in step S108, the infected asymptomatic people movement-tracing apparatus (not illustrated) may distribute the confirmed case traffic line information to the plurality of voice recognition terminals to form a confirmed case contact pool. Further, the infected asymptomatic people movement-tracing apparatus (not illustrated) may find an intersection between confirmed case contact pools generated by different confirmed cases. Further, the infected asymptomatic people movement-tracing apparatus (not illustrated) may backwardly track on the confirmed case contact pool to find out the infection route on the basis of the intersection between the acquired confirmed case contact pools. Further, the infected asymptomatic people movement-tracing apparatus (not illustrated) may select all the tracing targets on the infection route as subjects of self-quarantine.

Hereinafter, an operation flow of forming a confirmed case contact pool will be described in brief based on the above-detailed description.

According to an exemplary embodiment, in step S201 in the step of forming a confirmed case contact pool included in the step S108, the infected asymptomatic people searching unit 55a may provide the traffic line information of the confirmed case to the plurality of voice recognition terminals 17. The plurality of voice recognition terminals 17 may check whether the traffic line information of the confirmed case and the traffic line information of the tracing target match and when the traffic line information matches, provide the tracing targets to the infected asymptomatic people searching unit 55a.

In step S202, the infected asymptomatic people searching unit 55a may collect and store the traffic line information of the tracing targets provided in step S201 to form a cycle 1 confirmed case contact pool.

In step S203, the infected asymptomatic people searching unit 55a may provide the cycle 1 confirmed case contact pool obtained in step S202 to the plurality of voice recognition terminals 17. The plurality of voice recognition terminals 17 may check whether the traffic line information of the cycle 1 confirmed case contact pool and the traffic line information of the tracing target match and report the tracing targets having the matching traffic line to the infected asymptomatic people searching unit 55a.

In step S204, the infected asymptomatic people searching unit 55a may collect and store the traffic line information of the tracing targets reported in step S203 to form a cycle 2 confirmed case contact pool.

In step S205, when the above steps are repeatedly performed to obtain a cycle (N−1) confirmed case contact pool, the infected asymptomatic people searching unit 55a may provide the cycle (N-1) confirmed case contact pool to the plurality of voice recognition terminals 17. The plurality of voice recognition terminals 17 checks whether the traffic line information of the confirmed case contact pool and the tracing target matches to report the tracing target with the matching traffic line to the infected asymptomatic people searching unit 55a and the infected asymptomatic people searching unit 55a collects and stores the traffic line information of the reported tracing targets to form an N-th cycle confirmed case contact pool.

In step S206, the infected asymptomatic people searching unit 55a may generate an entire confirmed pool by a union of the first cycle confirmed case contact pool to N-th cycle confirmed case contact pool.

In the above description, steps S101 to S108 may be further divided into additional steps or combined as smaller steps depending on an implementation example of the present disclosure. Further, some steps may be omitted if necessary and the order of steps may be changed.

The infected asymptomatic people movement-tracing method according to the exemplary embodiment of the present disclosure may be implemented as a program command which may be executed by various computers to be recorded in a computer readable medium. The computer readable medium may include solely a program command, a data file, and a data structure or a combination thereof. The program command recorded in the medium may be specifically designed or constructed for the present disclosure or known to those skilled in the art of a computer software to be used. An example of the computer readable recording medium includes magnetic media, such as a hard disk, a floppy disk, and a magnetic tape, optical media, such as a CD-ROM and a DVD, magneto-optical media, such as a floptical disk, and a hardware device, such as a ROM, a RAM, a flash memory, specially formed to store and execute a program command. Examples of the program command include not only a machine language code which is created by a compiler but also a high level language code which may be executed by a computer using an interpreter. The hardware device may operate as one or more software modules in order to perform the operation of the present disclosure and vice versa.

Further, the infected asymptomatic people movement-tracing method may also be implemented as a computer program or an application executed by a computer which is stored in a recording medium.

The above description of the present disclosure is illustrative only and it is understood by those skilled in the art that the present disclosure may be easily modified to another specific type without changing the technical spirit of an essential feature of the present disclosure. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present disclosure is represented by the claims to be described below rather than the detailed description, and it is to be interpreted that the meaning and scope of the claims and all the changes or modified forms derived from the equivalents thereof come within the scope of the present disclosure.

What is claimed is:

1. An artificial intelligence-infected asymptomatic people movement-tracing apparatus, comprising:
   a digital communication module which is separate from a cellular phone of a tracing target and is installed in one region in a residence of the tracing target and provides communication with a disease control authority terminal or wireless communication connection with the cellular phone of the tracing target;
   a traffic line matching determining circuitry which compares confirmed case traffic line information and tracing target traffic line information to find out whether there is a route in which confirmed case traffic line information and tracing target traffic line information overlap;
   a controller which selects the tracing target as a subject of self-quarantine when there is a route in which the confirmed case traffic line information and the tracing target traffic line information overlap and controls driving of the digital communication module to provide information about the selected subject of self-quarantine to the disease control authority terminal;
   a confirmed case contact pool which is installed in the disease control authority terminal, from among a plurality of traffic line information of the cellular phone of the tracing target provided, to store only the traffic line information of the tracing target that overlaps the traffic line information of each confirmed case;
   an infected asymptomatic people searching circuitry which finds infected asymptomatic people by discovering an intersection between different confirmed case contact pools; and
   an infection route tracking circuitry which backwardly tracks the confirmed case contact pool to find out the infection route on the basis of information of the infected asymptomatic people included in the intersection.

2. The artificial intelligence-infected asymptomatic people movement-tracing apparatus according to claim 1, wherein the confirmed case traffic line information includes one or more location information selected from a GPS coordinate which is collectable from a confirmed case cellular phone, accessed base station information, a visit place QR code, a plurality of Key codes, a Bluetooth transmitter ID, and Wi-Fi ID access recording information and length of stay information on the traffic line of the confirmed case which is synchronized according to the location information.

3. The artificial intelligence-infected asymptomatic people movement-tracing apparatus according to claim 1, wherein the tracing target traffic line information includes one or more location information selected from a GPS coordinate which is collectable from a tracing target cellular phone, accessed base station information, a visit place QR code, a plurality of Key codes, a Bluetooth transmitter ID, and Wi-Fi ID access recording information and length of stay information which is synchronized according to the location information.

4. The artificial intelligence-infected asymptomatic people movement-tracing apparatus according to claim 1, further comprising:
   a traffic line tracing management application which is installed in the cellular phone of the tracing target and provides cellular phone location information of the tracing target to the digital communication module,
   wherein the traffic line tracing management application includes: a stay valid filter which extracts only the location information which is acquired for a predetermined time or longer, among a plurality of location information of the cellular phone of the tracing target provided from a plurality of location information providing circuitries as valid location information to cumulatively store the valid location information in a resident memory of the cellular phone of the tracing target.

5. The artificial intelligence-infected asymptomatic people movement-tracing apparatus according to claim 4, wherein the traffic line tracing management application further includes:
  a communication connection checking circuitry which detects a key code by a short-distance beacon, an ID of a Bluetooth transmitter, and a Wi-Fi ID of an access point (AP) from the cellular phone of the tracing target to store as the location information of the tracing target on the resident memory.

6. The artificial intelligence-infected asymptomatic people movement-tracing apparatus according to claim 4, wherein the plurality of location information providing circuitries includes at least one of a GPS (global positioning system) which provides location data of the cellular phone using a satellite, a Bluetooth transmitter or a Bluetooth beacon which provides a unique ID of Bluetooth to the cellular phone, cellular phones of short-distance contacts which share Key codes by the Bluetooth beacon, an access point (AP) of a wireless LAN which provides a Wi-Fi ID to the cellular phone, a black and white grid pattern which provides a QR code of a visit place to the cellular phone, and a base station which provides mobile communication location information accessing the cellular phone and includes a building address represented to be combined with building information provided by geographic information system (GIS) building-integrated information.

7. The artificial intelligence-infected asymptomatic people movement-tracing apparatus according to claim 4, wherein the traffic line tracing management application includes a self-quarantine confirming circuitry which confirms the tracing target as a self-quarantine and the self-quarantine confirming circuitry confirms the tracing target as the subject of self-quarantine when the controller or the disease control authority terminal provides self-quarantine subject confirmation notice information to the cellular phone of the tracing target who is determined as the subject of self-quarantine and the tracing target finishes a fingerprint authentication procedure for the notice information by means of the cellular phone.

8. An artificial intelligence-infected asymptomatic people movement-tracing apparatus, comprising:
  a voice recognition terminal which is separate from a cellular phone of a tracing target and is installed in one region in a residence of a tracing target, is connected to an external device, controls the external device by a voice instruction collected by a microphone, and provides a voice feedback service through a speaker,
  wherein the voice recognition terminal includes:
  a traffic line matching determining circuitry which compares traffic line information of a confirmed case and traffic line information of the tracing target to find out whether there is a route in which the traffic line of the tracing target overlaps the traffic line of the confirmed case; and
  a controller which selects the tracing target as a subject of self-quarantine when there is a route in which the traffic line information of the confirmed case and the traffic line information of the tracing target overlap and drives a digital communication module to transmit the information about the selected subject of self-quarantine to a disease control authority terminal;
  the disease control authority terminal includes:
  a confirmed case contact pool which stores information of the tracing targets having traffic lines which overlap the traffic line of the confirmed case from a plurality of voice recognition terminals;
  an infected asymptomatic people searching circuitry which finds an infected asymptomatic people by an intersection between the confirmed case contact pools formed by different confirmed cases; and
  an infection route tracking circuitry which backwardly tracks the confirmed case contact pools to find out the infection route on the basis of information of the infected asymptomatic people included in the intersection, and
  the cellular phone of the tracing target uploads cellular phone location information of the tracing target to the voice recognition terminal by connection with the digital communication module at every predetermined time.

9. The artificial intelligence-infected asymptomatic people movement-tracing apparatus according to claim 8, wherein the confirmed case contact pool provides the traffic line information of the confirmed case to the plurality of voice recognition terminals, the plurality of voice recognition terminals checks whether the traffic line information of the confirmed case and the traffic line information of the tracing target match, and provides the tracing targets to the infected asymptomatic people searching circuitry when the traffic line information match,
  the infected asymptomatic people searching circuitry collects and stores the provided traffic line information to form a first cycle confirmed case contact pool and provides the first cycle confirmed case contact pool to the plurality of voice recognition terminals,
  the plurality of voice recognition terminals checks whether the traffic line information match between the provided first cycle confirmed case contact pool and then the tracing target and reports the tracing targets having the matched traffic lines to the infected asymptomatic people searching circuitry, and
  the infected asymptomatic people searching circuitry collects and stores the reported traffic line information to a second cycle confirmed case contact pool and then forms an N-th cycle confirmed case pool to generate a union of first cycle to N-th cycle confirmed case contact pools.

10. The artificial intelligence-infected asymptomatic people movement-tracing apparatus according to claim 8, wherein the voice recognition terminal includes:
  a body temperature check diagnosis circuitry which determines a body temperature suspicious target on the basis of information collected from the tracing target; and
  a fingerprint authentication circuitry which checks whether a fingerprint information input from a fingerprint sensor matches a previously registered fingerprint information of the tracing target to perform identity authentication, and
  the body temperature check diagnosis circuitry includes:
  a non-contact temperature sensor including a thermal imaging camera which detects a thermal radiation emitted from a body of the tracing target to provide a thermal image or an IR temperature sensor which detects an IR ray emitted from the body of the tracing target to measure a temperature; and
  a body temperature determining circuitry which determines as an abnormal temperature suspicious target on the basis of a measured temperature value of a patient from the non-contact temperature sensor.

11. The artificial intelligence-infected asymptomatic people movement-tracing apparatus according to claim 1 or 8, wherein the cellular phone of the tracing target includes a building stay section setting circuitry, and
the building stay section setting circuitry calculates a length of stay and a visit location that the cellular phone of the tracing target stays in a specific building by tracking location information provided from a location information providing circuitry and uploads cellular phone location information of the tracing target which is cumulatively stored in a resident memory of the cellular phone of the tracing target at a stay ending time of the specific building to a tracing target traffic line information memory.

12. The artificial intelligence-infected asymptomatic people movement-tracing apparatus according to claim 1 or 8, wherein the cellular phone of the tracing target includes a building stay section setting circuitry, and
the building stay section setting circuitry tracks a UUID (universally unique identifier) value and a received signal strength indicator (RSSI) value provided from a Bluetooth beacon by Bluetooth communication connection between the Bluetooth beacon installed in one region of the building and the cellular phone of the tracing target which is staying in a Bluetooth beacon signal region to calculate a length of stay and a visit location that the cellular phone of the tracing target stays in a specific building and uploads cellular phone location information of the tracing target which is cumulatively stored in a resident memory of the cellular phone of the tracing target at a stay ending time of the specific building to a tracing target traffic line information memory.

13. The artificial intelligence-infected asymptomatic people movement-tracing apparatus according to claim 1 or 8, wherein the cellular phone of the tracing target includes a Bluetooth switching circuitry and the Bluetooth switching circuitry forcibly temporally switches the cellular phone to a Bluetooth mode whenever a location of the cellular phone of the tracing target in the unit of buildings is changed, and then searches for a Bluetooth beacon which is communicable with the cellular phone of the tracing target, collects unique ID information of a searched Bluetooth transmitter, stores location information which is associated with time information synchronized with the unique ID information of the Bluetooth transmitter in a resident memory on the cellular phone.

14. The artificial intelligence-infected asymptomatic people movement-tracing apparatus according to claim 8, wherein the voice recognition terminal includes:
a medical data receiver which receives medical data measured from a plurality of medical devices by short-distance communication connection between the digital communication module and the plurality of medical devices; and
an artificial intelligence neural network which has been deep-learning trained by the medical data for learning in advance, and
the deep learning trained artificial intelligence neural network analyzes the medical data received by the medical data receiver to automatically determine whether a patient has a disease and a risk of the disease.

15. The artificial intelligence-infected asymptomatic people movement-tracing apparatus according to claim 14, wherein the voice recognition terminal includes a digital TV or a smart mirror to share a screen between a patient and a medical expert during a remote medical diagnosis, the controller controls driving of the digital TV or the smart mirror to determine a necessity of the remote medical diagnosis according to a health condition of the patient on the basis of a medical data analysis result provided from the artificial intelligence neural network and perform the remote medical diagnosis between a doctor and the patient.

16. An infected asymptomatic people movement-tracing method performed by the artificial intelligence-infected asymptomatic people movement-tracing apparatus according to claim 1 or claim 8, comprising:
transmitting traffic line information of a tracing target stored in a resident memory on a cellular phone of the tracing target;
transmitting confirmed case traffic line information by a disease control authority terminal when a confirmed case occurs;
reporting the tracing target as a subject of self-quarantine to the disease control authority terminal when the traffic line information of the tracing target and the traffic line information of the confirmed case overlap;
transmitting self-quarantine subject confirmation notice information to the cellular phone of the tracing target from the disease control authority terminal;
confirming as the subject of self-quarantine when the tracing targets finish an authentication procedure for the notice information by a fingerprint authentication procedure provided to the cellular phone;
automatically finding out infected asymptomatic people information on the basis of an intersection between a plurality of confirmed case contact pools; and
finding out an infection route by backwardly tracking infected asymptomatic information included in the intersection on the confirmed case contact pool and notifying additional confirmation to the tracing targets included in the infection route as the subjects of self-quarantine.

17. An infected asymptomatic people movement-tracing method performed by the artificial-intelligence infected asymptomatic people movement-tracing apparatus according to claim 1 or claim 8, comprising:
allowing an infected asymptomatic people searching circuitry to distribute confirmed case traffic line information to a plurality of voice recognition terminals to form a confirmed case contact pool;
searching an intersection between the confirmed case contact pools generated by different confirmed cases;
finding out an infection route by backwardly tracking on each confirmed case contact pool, on the basis of the intersection between the confirmed case contact pools acquired in the searching; and
selecting all tracing targets on the infection route as subjects of self-quarantine.

18. The infected asymptomatic people movement-tracing method according to claim 17, wherein the searching of an intersection includes:
finding out a set Intersection_Index of a cycle (i, j) which generates the intersection; and
finding out a cycle ($i_o$, $j_o$) which generates a first intersection, and the finding out of a set Intersection_Index includes

```
Intersection....Index = [ ]
  for i = 1: max(i)
      for j = 1:: max(j)
          if TP₁ⁱ(A) ∩ TP₁ʲ(B) ≠ ∅
              include (i,j) in the set of Intersection_Index
          end
      end
  end,
``` here, i of (i, j) included in Intersection_Index is a cycle of a confirmed case A contact pool at a time when the intersection is generated and j is a cycle of a confirmed case B contact pool at a time when the intersection is generated, the finding out of a cycle $(i_o, j_o)$ which generates a first intersection finds out at least one or more of $(i_o, j_o)$ selected from $$(i_o, j_o) = \min_{i,j} \text{size}[TP_1^i(A) \cap TP_1^j(B) | \forall (i, j) \in \text{Intersection\_Index}]$$

or $$(i_o, j_o) = \min_{i,j} [(i + j) | \forall (i, j) \in \text{Intersection\_Index}]$$

or $$(i_o, j_o) = \min_{i,j} [\text{absolute}(i - j) | \forall (i, j) \in \text{Intersection\_Index}]$$

or $$(i_o, j_o) = \min_{i,j} [\min(i, j) | \forall (i, j) \in \text{Intersection\_Index}]$$

or $$(i_o, j_o) = \min_{i,j} [\max(i, j) | \forall (i, j) \in \text{Intersection\_Index}],$$

or here, $\forall(i,j) \in$ Intersection_Index refers to all (i, j) included in the set Intersection_Index, min (i,j) refers a minimum value between i and j, max (i,j) refers to a maximum value between i and j, absolute (i-j) refers an absolute value of (i-j), and size $[TP_1^i(A) \cap TP_1^j(B)]$ refers to a size of the intersection formed between $TP_1^i(A)$ and $TP_1^j(B)$.

19. The infected asymptomatic people movement-tracing method according to claim 18, wherein values of max(i) and max(j) are increased in proportional to an increase of the confirmed cases, increased in proportional to the increase of the confirmed cases whose infection routes are not known, or increased in proportional to a basic reproduction number (basic reproductive ratio) R0(R naught).

20. The infected asymptomatic people movement-tracing method according to claim 17, wherein the forming of a confirmed case contact pool includes:

allowing the infected asymptomatic people searching circuitry to provide the traffic line information of the confirmed case to the plurality of voice recognition terminals, a plurality of voice recognition terminals to check whether the traffic line information of the confirmed case and the traffic line information of the tracing target match, and provide the tracing targets to the infected asymptomatic people searching unit when the traffic line information match;

allowing the infected asymptomatic people searching circuitry to collect and store the traffic line information of the tracing targets provided in the providing to the infected asymptomatic people searching circuitry to form a first cycle confirmed case contact pool;

providing the first cycle confirmed case contact pool to the plurality of voice recognition terminals, allowing the plurality of voice recognition terminals to check whether traffic line information between the first cycle confirmed case contact pool and the tracing target match to report the matched tracing targets to the infected asymptomatic people searching circuitry;

allowing the infected asymptomatic people searching circuitry to collect and store the traffic line information of the reported tracing targets to form a second cycle confirmed case contact pool;

allowing the infected asymptomatic people searching circuitry to provide an (N−1)th cycle confirmed case contact pool to the plurality of voice recognition terminals, the plurality of voice recognition terminals to check whether the traffic line information of the confirmed case contact pool and the traffic line information of the tracing target match, and report the matched tracing targets to the infected asymptomatic people searching circuitry, and infected asymptomatic people searching circuitry to collect and store the traffic line information of the reported tracing targets to form an N-th cycle confirmed case contact pool; and generating an entire confirmed case pool by a union of the first cycle confirmed case contact pool to the N-th cycle confirmed case contact pool.

\* \* \* \* \*